United States Patent
Wünsch et al.

(10) Patent No.: US 8,309,725 B2
(45) Date of Patent: Nov. 13, 2012

(54) PERHYDROQUINOXALINE DERIVATIVES, THEIR PREPARATION AND USE IN MEDICAMENTS

(75) Inventors: Bernhard Wünsch, Münster (DE); Dirk Schepmann, Münster (DE); Christian Bourgeois, Selm (DE)

(73) Assignee: Dr. August Wolff GmbH & Co. KG—Arzneimittel, Bielefeld (DE)

( * ) Notice: Subject to any disclaimer, the term of this patent is extended or adjusted under 35 U.S.C. 154(b) by 126 days.

(21) Appl. No.: 12/809,243

(22) PCT Filed: Dec. 19, 2008

(86) PCT No.: PCT/EP2008/068000
§ 371 (c)(1),
(2), (4) Date: Jun. 18, 2010

(87) PCT Pub. No.: WO2009/080745
PCT Pub. Date: Jul. 2, 2009

(65) Prior Publication Data
US 2010/0311761 A1    Dec. 9, 2010

(30) Foreign Application Priority Data
Dec. 20, 2007  (DE) .......................... 10 2007 062 550

(51) Int. Cl.
C07D 241/36  (2006.01)
(52) U.S. Cl. ....................................... 544/355; 548/518
(58) Field of Classification Search ................. 544/355; 548/518
See application file for complete search history.

(56) References Cited

U.S. PATENT DOCUMENTS

| 6,303,611 B1 | 10/2001 | Zhang et al. |
| 6,355,641 B1 | 3/2002 | Coffen et al. |
| 2002/0042399 A1 | 4/2002 | Kruse et al. |

FOREIGN PATENT DOCUMENTS

WO    00/55143 A1    9/2000

OTHER PUBLICATIONS

Giardinà, D., et al. "Synthesis and Biological Profile of the Enantiomers of [4-(4-Amino-6,7-dimethoxyquinazolin-2-yl)-cis-octahydroquinoxalin-1-yl]furan-2-ylmethanone (Cyclazosin), a Potent Competitive α1B-Adrenoceptor Antagonist". J. Med. Chem. 1996, vol. 39, pp. 4602-4607.

Rees, D.C. "Synthesis of Perhydro-2(1H)-quinoxalinones and Perhydropyrrolo[1,2-α]quinoxalin-4(5H)-one Derivatives". Journal of Heterocyclic Chemistry. 1987, vol. 24, pp. 1297-1300.

*Primary Examiner* — Douglas M Willis
(74) *Attorney, Agent, or Firm* — Nath, Goldberg & Meyer; Tanya E. Harkins

(57) ABSTRACT

The present subject matter relates to perhydroquinoxaline derivates, processes for their preparation, their use for the preparation of a medicament and medicaments containing perhydroquinoxaline derivates. The perhydroquinoxaline derivates presently disclosed are those according to the general formula 1:

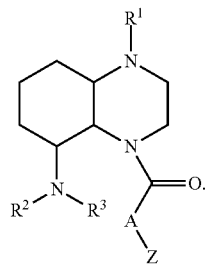

(1)

6 Claims, No Drawings

PERHYDROQUINOXALINE DERIVATIVES, THEIR PREPARATION AND USE IN MEDICAMENTS

CROSS-REFERENCE TO RELATED APPLICATIONS

This is a National Phase Application filed under 35 U.S.C. §371 as a national stage of PCT/EP2008/068000, filed on Dec. 19, 2008, claiming the benefit of German Patent Application 10 2007 062 550.4, filed on Dec. 20, 2007, the content of each of which is hereby incorporated by reference in its entirety.

The present invention relates to perhydroquinoxaline derivatives and medicaments containing perhydroquinoxaline derivatives.

Pain is an unpleasant perceptive or sensorial experience which has a vital protective and warning function and may be accompanied by actual or imminent tissue damage. Depending on its development, pain perception is differentiated, for example, into peripheral or central pain.

FIELD OF INVENTION

Pain is signaled to be body via receptors in the nervous system, the patient's pain sensation being subjective.

BACKGROUND

Treatment of pain is of great importance in medicine. Analgesic agents as a rule act by blocking opioid receptors. Conventional opioids, such as morphine, are thus opioid analgesics which are often employed in clinical pain therapy because of their potent analgesic action. These selectively activate the μ receptor. However, undesirable side effects of such pain therapy are sometimes considerable centrally mediated side effects, such as respiratory depression, vomiting and bradycardia. Possible psycho-dependencies are furthermore a disadvantage.

In view of the large number of types of pain and diseases associated with pain, there is a great need for active analgesics.

BRIEF SUMMARY

The invention was based on the object of providing an agent which overcomes at least one of the abovementioned disadvantages of the prior art. In particular, the object was to provide novel compounds which can be used as pharmaceutical active compounds, in particular for combating pain.

This object is achieved by compounds according to the general formula (I) as shown below and/or racemates, enantiomers, diastereomers, solvates, hydrates thereof and pharmaceutically acceptable salts and/or esters thereof:

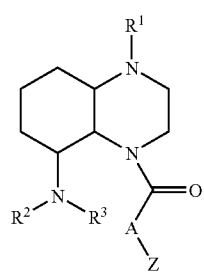

(1)

wherein:
$R^1$ is chosen from the group comprising H; $C_1$-$C_{10}$-alkyl; $C_3$-$C_{10}$-cycloalkyl; COO($C_1$-$C_{10}$-alkyl); $C_1$-$C_6$-alkoxycarbonyl; $C_1$-$C_6$-oxocarbonyl;
phenylalkyl with $C_1$-$C_6$-alkyl, wherein the phenyl radical can be substituted by one or more identical or different groups chosen from the group comprising halogen, $C_1$-$C_6$-alkyloxy, $NH_2$, NH($C_1$-$C_5$-alkyl), N($C_1$-$C_5$-alkyl)$_2$, OH, $SO_2$($C_1$-$C_5$-alkyl), SO($C_1$-$C_5$-alkyl), $CF_3$, CN, $NO_2$, $SO_2$N($C_1$-$C_5$-alkyl)$_2$, $SO_2NH_2$, $SO_2$NH($C_1$-$C_5$-alkyl), $SO_2$NH(aryl), $SO_2$NH(phenyl) and/or $SO_2$NH(heteroaryl);
$C_1$-$C_{10}$-acyl; $C_3$-$C_{10}$-cycloacyl; phenylacyl, wherein the acyl radical is a $C_1$-$C_6$-acyl radical and the phenyl radical can be substituted by one or more identical or different groups chosen from the group comprising halogen, $C_1$-$C_6$-alkyloxy, $NH_2$, NH($C_1$-$C_5$-alkyl), N($C_1$-$C_5$-alkyl)$_2$, OH, $SO_2$($C_1$-$C_5$-alkyl), SO($C_1$-$C_5$-alkyl), $CF_3$, CN, $NO_2$, $SO_2$N($C_1$-$C_5$-alkyl)$_2$, $SO_2NH_2$, $SO_2$NH($C_1$-$C_5$-alkyl), $SO_2$NH(aryl), $SO_2$NH(phenyl) and/or $SO_2$NH(heteroaryl);
mono-, bi- or tricyclic heteroaryl containing one, two, three or four hetero atoms chosen from the group comprising N, O and/or S;
mono-, bi- or tricyclic heteroarylalkyl containing one, two, three or four hetero atoms chosen from the group comprising N, O and/or S, wherein the alkyl radical is a $C_1$-$C_6$ alkyl radical;
mono-, bi- or tricyclic heteroarylacyl containing one, two, three or four hetero atoms chosen from the group comprising N, O and/or S, wherein the acyl radical is a $C_1$-$C_6$-acyl radical;
C(O)($C_1$-$C_{10}$-alkyl); C(O)N($C_1$-$C_{10}$-alkyl)$_2$; C(O)($C_3$-$C_{10}$-cycloalkyl); COO($C_1$-$C_{10}$-alkyl); COO(aryl); COO($C_3$-$C_{10}$-cycloalkyl);
C(O)COO($C_1$-$C_{10}$-alkyl); C(O)—(CH$_2$)$_q$—COOH, wherein q is 0, 1, 2, 3 or 4; C(O)—(CH$_2$)$_r$—COO($C_1$-$C_{10}$-alkyl), wherein r is 0, 1, 2, 3 or 4; C(O)—CH(NH$_2$)—(CH$_2$)$_s$—COOH, wherein s is 0, 1, 2, 3 or 4; C(O)—CH(NH$_2$)—(CH$_2$)$_t$—COO($C_1$-$C_{10}$-alkyl), wherein t is 0, 1, 2, 3 or 4; C(O)—(CH$_2$)$_u$—CH(NH$_2$)—COOH, wherein u is 0, 1, 2, 3 or 4 and/or C(O)—(CH$_2$)$_v$—CH(NH$_2$)—COO($C_1$-$C_{10}$-alkyl), wherein v is 0, 1, 2, 3 or 4;
$R^2$, $R^3$ are in each case identical or independent of each other and are chosen from the group comprising H; $C_1$-$C_{10}$-alkyl; $C_3$-$C_{10}$-cycloalkyl; phenylalkyl with $C_1$-$C_6$-alkyl and wherein the phenyl radical can be substituted by one or more identical or different groups chosen from the group comprising halogen, $C_1$-$C_5$-alkyl, $C_1$-$C_4$-alkyloxy, $NH_2$, NH($C_1$-$C_5$-alkyl), N($C_1$-$C_5$-alkyl)$_2$, OH, COOH, COO($C_1$-$C_{10}$-alkyl), $CONH_2$, CONH($C_1$-$C_{10}$-alkyl), CON($C_1$-$C_{10}$-alkyl)$_2$, $SO_2$($C_1$-$C_5$-alkyl), $SO_2$HN($C_1$-$C_5$-alkyl), $CF_3$, CN and/or $NO_2$, or
$R^2$ and $R^3$ form, together with the nitrogen to which they are bonded, a saturated 3- to 8-membered N-heterocycle, wherein this can be substituted by one or more identical or different groups chosen from the group comprising OH, $C_1$-$C_4$-alkyloxy, carbonyl oxygen, $NH_2$, NH($C_1$-$C_5$-alkyl), N($C_1$-$C_5$-alkyl)$_2$, COOH, COO($C_1$-$C_{10}$-alkyl), $CONH_2$, CONH($C_1$-$C_{10}$-alkyl), CON($C_1$-$C_{10}$-alkyl)$_2$, $OPO_3H_2$, $OSO_3H$, $SO_2$($C_1$-$C_5$-alkyl), $SO_2$HN($C_1$-$C_5$-alkyl), CN, O-arylacetyl, O-phenylacetyl, arylacetoxy and/or acetylbenzyl, which can be substituted by two Cl groups;

A is chosen from the group comprising $(CH_2)_n$, wherein n is 0, 1, 2, 3, 4, 5 or 6; $C_2$-$C_5$-alkylene, which can be substituted by at least one $C_1$-$C_3$-alkyl radical; O; S; NH and/or aryl;

Z is chosen from the group comprising H; $NH_2$; COOH; COO($C_1$-$C_5$-alkyl); CH($NH_2$)COOH; $C_1$-$C_6$-acyl; $C_1$-$C_6$-alkoxycarbonyl; $C_1$-$C_6$-oxocarbonyl;

phenyl, which can be substituted by one or more identical or different groups chosen from the group comprising halogen, $C_1$-$C_5$-alkyl, $C_1$-$C_5$-alkyloxy, $NH_2$, NH($C_1$-$C_5$-alkyl), N($C_1$-$C_5$-alkyl)$_2$, OH, $SO_2$($C_1$-$C_5$-alkyl), SO($C_1$-$C_5$-alkyl), $CF_3$, CN, $NO_2$, $SO_2$N($C_1$-$C_5$-alkyl)$_2$, $SO_2NH_2$, $SO_2$NH($C_1$-$C_5$-alkyl), $SO_2$NH(aryl), $SO_2$NH(phenyl) and/or $SO_2$NH(heteroaryl);

a mono-, bi- or tricyclic aryl or heteroaryl containing one, two, three or four hetero atoms chosen from the group comprising N, O and/or S, wherein the aryl or heteroaryl group can be substituted by one or more identical or different groups chosen from the group comprising halogen, $C_1$-$C_4$-alkyloxy, $NH_2$, NH($C_1$-$C_5$-alkyl), N($C_1$-$C_5$-alkyl)$_2$, OH, $SO_2$($C_1$-$C_5$-alkyl), SO($C_1$-$C_5$-alkyl), $CF_3$, CN, $NO_2$, $SO_2$N($C_1$-$C_5$-alkyl)$_2$, $SO_2NH_2$, $SO_2$NH($C_1$-$C_5$-alkyl), $SO_2$NH(aryl), $SO_2$NH(phenyl) and/or $SO_2$NH(heteroaryl).

DETAILED DESCRIPTION

It has been found, surprisingly, that the compounds according to the invention can have an analgesic action. A particular advantage of the compounds according to the invention is the fact that the compounds can have an analgesic action predominantly in the peripheral system.

Without being tied to a particular theory, it is assumed that the perhydroquinoxaline ring structure of the compounds according to the invention has a considerable influence on the advantageous properties of the compounds.

In the context of the present invention, unless stated otherwise, the term "heteroaryl" is to be understood as meaning mono-, bi- or tricyclic heteroaryl containing one, two, three or four hetero atoms chosen from the group comprising N, O and/or S.

Preferred heteroaryl radicals are chosen from the group comprising pyridinyl, pyrimidinyl, pyrazinyl, triazolyl, pyridazinyl, 1,3,5-triazinyl, quinolyl, isoquinolyl, quinolinyl, isoquinolinyl, quinoxalinyl, imidazolyl, pyrazolyl, benzimidazolyl, benzooxazolyl, benzothiazolyl, thiazolyl, oxazolyl, isoxazolyl, oxazolidinyl, pyrrolyl, carbazolyl, indolyl, isoindolyl, furyl, benzofuryl, benzofuranyl, 1,3-benzodioxolyl, thienyl and/or benzothienyl.

Particularly preferred heteroaryl radicals are chosen from the group comprising pyridinyl, thiazolyl, oxazolyl, isoxazolyl, imidazolyl, indolyl, quinolyl, isoquinolyl, benzofuranyl, 1,3-benzodioxolyl, benzothienyl, benzimidazolyl, benzooxazolyl, benzothiazolyl, furyl and/or thienyl.

Preferred heteroaryl radicals are mononuclear heteroaryl radicals. Particularly preferred heteroaryl radicals are mononuclear heteroaryl radicals having 4, 5 or 6 carbon atoms.

Further preferred heteroaryl radicals are mononuclear heteroaryl radicals, in particular chosen from the group comprising 2-pyridyl, 3-pyridyl, 4-pyridyl, furyl, thienyl, imidazolyl, pyrimidinyl and/or oxazolyl.

In the context of this invention, for the substituent pyridine the designation "pyridinyl" and also the more common abbreviated form "pyridyl" are used synonymously.

In preferred embodiments of the structural element $R^1$, the heteroarylalkyl group is —$(CH_2)_m$-heteroaryl, wherein m is 0, 1, 2, 3 or 4.

In further preferred embodiments of the structural element $R^1$, the heteroarylacyl group is —CO—$(CH_2)_p$-heteroaryl, wherein p is 0, 1, 2, 3 or 4.

In embodiments of the structural element $R^1$ which are furthermore preferred, C(O)—$(CH_2)_q$—COOH, wherein q is 0, 1, 2, 3 or 4, is chosen from the group comprising C(O)COOH, C(O)—$CH_2$—COOH and/or C(O)—$(CH_2)_2$—COOH.

In further preferred embodiments of the structural element $R^1$, C(O)—$(CH_2)_r$—COO($C_1$-$C_{10}$-alkyl), wherein r is 0, 1, 2, 3 or 4, is chosen from the group comprising C(O)—$CH_2$—COO—$CH_3$, C(O)—$CH_2$—COO—$C_2H_5$, C(O)—$(CH_2)_2$—COO—$CH_3$ and/or C(O)—$(CH_2)_2$—COO—$C_2H_5$.

In further preferred embodiments of the structural element $R^1$, C(O)—CH($NH_2$)—$(CH_2)_s$—COOH, wherein s is 0, 1, 2, 3 or 4, is C(O)—CH($NH_2$)—$CH_2$—COOH.

In further preferred embodiments of the structural element $R^1$, C(O)—CH($NH_2$)—$(CH_2)_t$—COO($C_1$-$C_{10}$-alkyl), wherein t is 0, 1, 2, 3 or 4, is chosen from the group comprising C(O)—CH($NH_2$)—$CH_2$—COO—$CH_3$ and/or C(O)—$(CH_2)_2$—COO—$C_2H_5$.

In also further preferred embodiments of the structural element $R^1$, C(O)—$(CH_2)_u$—CH($NH_2$)—COOH, wherein u is 0, 1, 2, 3 or 4, is C(O)—$CH_2$—CH($NH_2$)—COOH.

In still further preferred embodiments of the structural element $R^1$, C(O)—$(CH_2)_v$—CH($NH_2$)—COO($C_1$-$C_{10}$-alkyl), wherein v is 0, 1, 2, 3 or 4, is chosen from the group comprising C(O)—$CH_2$—CH($NH_2$)—COO—$CH_3$ and/or C(O)—$(CH_2)_2$—COO—$C_2H_5$.

The term "$C_1$-$C_{10}$-alkyl" includes, unless stated otherwise, straight-chain, branched or cyclic alkyl groups, preferably chosen from the group comprising methyl, ethyl, propyl, butyl, pentyl, neopentyl, undecyl, dodecyl, pentadecyl, hexadecyl, heptadecyl, octadecyl and/or cyclohexyl. The term "$C_1$-$C_{10}$-alkyl" preferably includes straight-chain, branched or cyclic alkyl groups, preferably chosen from the group comprising methyl, ethyl, propyl, butyl, pentyl, neopentyl, hexyl, heptyl, octyl, nonyl and/or decyl.

$C_1$-$C_5$-alkyl groups are preferred. $C_1$-$C_5$-alkyl groups are preferably chosen from the group comprising methyl, ethyl, n-propyl, isopropyl, n-butyl, tert-butyl and/or n-pentyl. $C_1$-$C_5$-alkyl groups are particularly preferably chosen from the group comprising methyl, ethyl, n-propyl and/or isopropyl.

Regarding monoalkyl- and dialkylamino substituents NH($C_1$-$C_5$-alkyl) and/or N($C_1$-$C_5$-alkyl)$_2$, $C_1$-$C_5$-alkyl groups are preferably chosen from the group comprising methyl and/or ethyl.

$C_1$-$C_6$-alkyloxy groups are preferably chosen from the group comprising methoxy, ethoxy, linear or branched propoxy and/or butoxy.

The term "halogen" includes fluorine, chlorine, bromine and iodine, fluorine or chlorine being preferred, in particular chlorine.

The term "aryl" is preferably to be understood as meaning aromatic radicals having 6 to 20 C atoms, preferably phenyl, naphthyl, indenyl, biphenyl and 5- or 6-membered heterocyclic rings, which contain 1 to 3 hetero atoms chosen from O, N or S and are optionally fused with a benzene ring, such as indolyl. Phenyl and indolyl are preferred, in particular phenyl. The term "aryl" preferably includes carbocycles. Further preferred aryl groups are chosen from the group comprising phenyl, naphthyl and/or indenyl.

In the context of the present invention, the term "phenylalkyl" includes the group -alkylphenyl, wherein phenylalkyl includes, for example, phenylethyl and benzyl.

One advantage of the compounds according to the invention is that they can have a high affinity for the κ receptor. It is furthermore of particular advantage that in preferred embodiments, the compounds according to the invention have a high selectivity of binding to the κ receptor with respect to binding to μ, δ, $σ_1$ and $σ_2$ receptors and with respect to the phencyclidine (PCP) binding site of the NMDA receptor (NMDA: N-methyl D-aspartate).

An advantage of a high selectivity of binding to the κ receptor can be provided in that no or only mildly centrally mediated side effects occur. A particular advantage of a high selectivity of binding to the κ receptor can be provided in that it is possible to reduce the risk of a psycho-dependency.

In preferred embodiments of the structural elements $R^2$ and $R^3$, these form, together with the nitrogen to which they are bonded, a saturated 3- to 8-membered N-heterocycle. The saturated 3- to 8-membered N-heterocycle is preferably chosen from the group comprising pyrrolidinyl, piperazinyl, piperidinyl, morpholinyl and/or azepanyl. Preferred saturated N-heterocycles are 5- or 6-membered heterocyclic rings chosen from the group comprising pyrrolidinyl, piperazinyl, piperidinyl and/or morpholinyl.

In preferred embodiments, the structural elements $R^2$ and $R^3$ form, together with the nitrogen to which they are bonded, a pyrrolidinyl radical, wherein the pyrrolidinyl radical can be substituted by one or more identical or different groups chosen from the group comprising $C_1$-$C_5$-alkyl, $C_1$-$C_5$-alkyloxy and/or OH. Preferably, the pyrrolidinyl radical is substituted by one or two OH groups. Particularly preferably, the structural elements $R^2$ and $R^3$ form, together with the nitrogen to which they are bonded, a pyrrolidine or a 3-hydroxypyrrolidine ring.

The structural element A is preferably a group $(CH_2)_n$, wherein n is preferably 0 or 1. Preferably, n is 1.

The structural element Z is preferably a phenyl radical, which can be substituted by one or more identical or different groups chosen from the group comprising $C_1$-$C_5$-alkyl, $C_1$-$C_5$-alkyloxy, OH, halogen, preferably chosen from F, Cl, Br and/or I, $CF_3$, CN, $SO_2(C_1$-$C_5$-alkyl), $NO_2$, $NH_2$, $NH(C_1$-$C_5$-alkyl), and/or $N(C_1$-$C_5$-alkyl)$_2$. Preferably, the phenyl radical is substituted by one or two halogen atoms, preferably chosen from F, Cl, Br and/or I, preferably Cl.

A substitution of the phenyl radical by one, preferably two chlorine atoms can result in a considerable increase in the activity of the compound.

In preferred embodiments, the structural element C(O)AZ forms a phenylacetyl or a dichlorophenylacetyl group.

Preferred compounds and/or racemates, enantiomers, diastereomers, solvates, hydrates thereof and pharmaceutically acceptable salts and/or esters thereof have the following general formula (2):

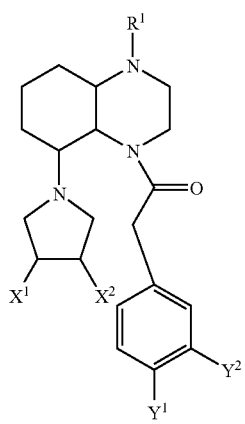

(2)

wherein:
$R^1$ is chosen from the group comprising H; $C_1$-$C_{10}$-alkyl; $C_3$-$C_{10}$-cycloalkyl; COO($C_1$-$C_{10}$-alkyl); $C_1$-$C_6$-alkoxycarbonyl; $C_1$-$C_6$-oxocarbonyl;
   phenylalkyl with $C_1$-$C_6$-alkyl, wherein the phenyl radical can be substituted by one or more identical or different groups chosen from the group comprising halogen, $C_1$-$C_6$-alkyloxy, $NH_2$, $NH(C_1$-$C_5$-alkyl), $N(C_1$-$C_5$-alkyl)$_2$, OH, $SO_2(C_1$-$C_5$-alkyl), $SO(C_1$-$C_5$-alkyl), $CF_3$, CN, $NO_2$, $SO_2N(C_1$-$C_5$-alkyl)$_2$, $SO_2NH_2$, $SO_2NH(C_1$-$C_5$-alkyl), $SO_2NH$(aryl), $SO_2NH$(phenyl) and/or $SO_2NH$(heteroaryl);
   $C_1$-$C_{10}$-acyl; $C_3$-$C_{10}$-cycloacyl; phenylacyl, wherein the acyl radical is a $C_1$-$C_6$-acyl radical and the phenyl radical can be substituted by one or more identical or different groups chosen from the group comprising halogen, $C_1$-$C_6$-alkyloxy, $NH_2$, $NH(C_1$-$C_5$-alkyl), $N(C_1$-$C_5$-alkyl)$_2$, OH, $SO_2(C_1$-$C_5$-alkyl), $SO(C_1$-$C_5$-alkyl), $CF_3$, CN, $NO_2$, $SO_2N(C_1$-$C_5$-alkyl)$_2$, $SO_2NH_2$, $SO_2NH(C_1$-$C_5$-alkyl), $SO_2NH$(aryl), $SO_2NH$(phenyl) and/or $SO_2NH$(heteroaryl);
   mono-, bi- or tricyclic heteroaryl containing one, two, three or four hetero atoms chosen from the group comprising N, O and/or S;
   mono-, bi- or tricyclic heteroarylalkyl containing one, two, three or four hetero atoms chosen from the group comprising N, O and/or S, and the alkyl radical is a $C_1$-$C_6$-alkyl radical;
   mono-, bi- or tricyclic heteroarylacyl containing one, two, three or four hetero atoms chosen from the group comprising N, O and/or S, and the acyl radical is a $C_1$-$C_6$-acyl radical; $C(O)(C_1$-$C_{10}$-alkyl; $C(O)N(C_1$-$C_{10}$-alkyl)$_2$; $C(O)(C_3$-$C_{10}$-cycloalkyl); $COO(C_1$-$C_{10}$-alkyl); COO(aryl); $COO(C_3$-$C_{10}$-cycloalkyl);
   $C(O)COO(C_1$-$C_{10}$-alkyl), $C(O)$—$(CH_2)_q$—COOH, wherein q is 0, 1, 2, 3 or 4, $C(O)$—$(CH_2)_r$—$COO(C_1$-$C_{10}$-alkyl), wherein r is 0, 1, 2, 3 or 4, $C(O)$—$CH(NH_2)$—$(CH_2)_s$—COOH, wherein s is 0, 1, 2, 3 or 4, $C(O)$—$CH(NH_2)$—$(CH_2)_t$—$COO(C_1$-$C_{10}$-alkyl), wherein t is 0, 1, 2, 3 or 4, $C(O)$—$(CH_2)_u$—$CH(NH_2)$—COOH, wherein u is 0, 1, 2, 3 or 4, and/or $C(O)$—$(CH_2)_v$—$CH(NH_2)$—$COO(C_1$-$C_{10}$-alkyl)$, wherein v is 0, 1, 2, 3 or 4;

$X^1$, $X^2$ are in each case identical or independent of each other and are chosen from the group comprising H, OH, carbonyl oxygen, $NH_2$, $NH(C_1$-$C_5$-alkyl), $N(C_1$-$C_5$-alkyl)$_2$, COOH, $COO(C_1$-$C_{10}$-alkyl), $CONH_2$, $CONH(C_1$-$C_{10}$-alkyl)$, $CON(C_1$-$C_{10}$-alkyl)$_2$, $OPO_3H_2$, $OSO_3H$, $SO_2(C_1$-$C_5$-alkyl), $SO_2HN(C_1$-$C_5$-alkyl), $C_1$-$C_4$-alkyloxy, O-arylacetyl, O-phenylacetyl, arylacetoxy and/or acetylbenzyl, which can be substituted by two Cl groups;

$Y^1$, $Y^2$ are in each case identical or independent of each other and are chosen from the group comprising H, halogen, $C_1$-$C_5$-alkyl, $C_1$-$C_5$-alkyloxy, $NH_2$, $NH(C_1$-$C_5$-alkyl), NH(aryl), NH(phenyl), NH(heteroaryl), $N(C_1$-$C_5$-alkyl)$_2$, OH, $SO_2(C_1$-$C_5$-alkyl), $SO(C_1$-$C_5$-alkyl), $CF_3$, CN, $NO_2$, $SO_2N(C_1$-$C_5$-alkyl)$_2$, $SO_2NH_2$, $SO_2NH(C_1$-$C_5$-alkyl).

The structural element $R^1$ is preferably chosen from the group comprising H, $C_1$-$C_5$-alkyl, phenylalkyl with $C_1$-$C_3$-alkyl and wherein the phenyl radical can be substituted by one or more identical or different groups chosen from the group comprising Cl, OH and/or $C_1$-$C_4$-alkyloxy, and/or N-heteroarylalkyl, wherein the N-heteroaryl radical is chosen from pyridinyl, pyrimidinyl, pyrazinyl and/or pyrrolyl, and the alkyl radical is a $C_1$-$C_3$-alkyl radical.

The structural element $R^1$ is further preferably chosen from the group comprising $C_1$-$C_3$-acyl, benzoyl, $COO(C_1$-$C_3$-alkyl), C(O)COOH, C(O)—$CH_2$—COOH, C(O)—$CH_2$—COO—$CH_3$ and/or C(O)—$CH_2$—COO—$C_2H_5$.

The structural elements $X^1$ and $X^2$ are preferably chosen from the group comprising H, OH and/or O-acetylphenyl, which is substituted by two Cl groups.

Preferably, at least one structural element $X^1$ or $X^2$ is H. Further preferably, one structural element $X^1$ or $X^2$ is OH. In preferred embodiments of the compound of the formula (2), the structural element $X^1$ is H and the structural element $X^2$ is OH.

The structural elements $Y^1$ and $Y^2$ are preferably chosen from the group comprising OH, F and/or Cl. In preferred embodiments of the compound of the formula (2), the structural elements $Y^1$ and $Y^2$ are Cl. A substitution by two groups Cl can result in a considerable increase in the activity of the compound. A great advantage which can be provided by the structural elements $Y^1$ and $Y^2$ being chlorine is that the compounds can have a particularly good affinity for the κ receptor.

Particularly preferred compounds and/or racemates, enantiomers, diastereomers, solvates, hydrates thereof and pharmaceutically acceptable salts and/or esters thereof have the following general formula (3):

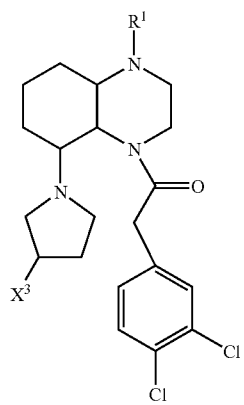

(3)

wherein:
R$^1$ is chosen from the group comprising H; $C_1$-$C_5$-alkyl;
  phenylalkyl with $C_1$-$C_4$-alkyl and wherein the phenyl radical can be substituted by one or more identical or different groups chosen from the group comprising Cl, OH and/or $C_1$-$C_4$-alkyloxy;
  N-heteroarylalkyl, wherein the N-heteroaryl radical is chosen from pyridinyl, imidazolyl, pyrimidinyl, pyrazinyl and/or pyrrolyl, and the alkyl radical is a $C_1$-$C_4$-alkyl radical;
  $C_1$-$C_5$-acyl; benzoyl; COO($C_1$-$C_5$-alkyl); COO(aryl);
  C(O)—(CH$_2$)$_q$—COOH, wherein q is 0, 1, 2, 3 or 4 and/or C(O)—(CH$_2$)$_r$—COO($C_1$-$C_5$-alkyl), wherein r is 0, 1, 2, 3 or 4;
$X^3$ is chosen from the group comprising H, OH, benzyl and/or O-arylacetyl, which can be substituted by two Cl groups.

The structural element $X^3$ is particularly preferably chosen from the group comprising H and/or OH.

The structural element $R^1$ is particularly preferably chosen from the group comprising H, methyl, butyl, pentyl, benzyl, p-methoxybenzyl, pyridinylmethyl, in particular 2-pyridinyl-methyl, 3-pyridinylmethyl and/or imidazolylmethyl. The structural element $R^1$ is very particularly preferably H.

The structural element $R^1$ is further preferably chosen from the group comprising benzoyl, acetyl, propionyl, COOCH$_3$, COOC$_2$H$_5$, C(O)COOH, C(O)—CH$_2$—COOH, C(O)—(CH$_2$)$_2$—COOH, C(O)—CH$_2$—COO—CH$_3$, C(O)—CH$_2$—COO—C$_2$H$_5$, C(O)—(CH$_2$)$_2$—COO—CH$_3$ and/or C(O)—(CH$_2$)$_2$—COO—C$_2$H$_5$.

In preferred embodiments, the structural element $R^1$ is an acyl radical chosen from the group comprising benzoyl, acetyl, propionyl, COOCH$_3$, COOC$_2$H$_5$, C(O)COOH, C(O)—CH$_2$—COOH and/or C(O)—CH$_2$—COO—CH$_3$ and the structural element $X^3$ is chosen from the group comprising H and/or OH.

Without being tied to a particular theory, it is assumed that the action of the compounds according to the invention in particular is based on the steric action of the perhydroquinoxaline group, in particular in combination with the structural element $R^1$. In particular, a combination of the perhydroquinoxaline group with a structural element $R^1$ which is an acyl radical or an alkyl radical can provide an advantageous analgesic action.

An advantage of the embodiments in which the structural element $R^1$ is an acyl radical chosen from the group comprising benzoyl, acetyl, propionyl, COOCH$_3$, COOC$_2$H$_5$, C(O)COOH, C(O)—CH$_2$—COOH and/or C(O)—CH$_2$—COO—CH$_3$ and the structural element $X^3$ is chosen from the group comprising H and/or OH is that these can have a good affinity for the κ receptor. For example, the $K_i$ value, as a measure of the affinity for the κ receptor, can be in the range of from $\geq 1$ nM to $\leq 800$ nM, preferably in the range of from $\geq 5$ nM to $\leq 600$ nM, preferably in the range of from $\geq 9$ nM to $\leq 500$ nM.

The $K_i$ value was determined by the method according to Hunter et al., Br. J. Pharmacol. 1990, 1001. 183-189 and Smith et al., J. Neuoch. 1989, 53, 27-36, wherein a preparation from the whole guinea pig brain was used and [$^3$H]-U-69,593 (Amersham) was used as the radioligand, as described in Example 30.

A particular advantage of the embodiments in which the structural element $R^1$ is an acyl radical chosen from the group comprising benzoyl, acetyl, propionyl, COOCH$_3$, COOC$_2$H$_5$, C(O)COOH, C(O)—CH$_2$—COOH and/or C(O)—CH$_2$—COO—CH$_3$ and the structural element $X^3$ is chosen from the group comprising H and/or OH is that these can have a good selectivity of binding to the κ receptor with respect to binding to the μ receptor.

In further preferred embodiments, the structural element $R^1$ is a phenylalkyl, alkyl, heteroaryl or heteroarylalkyl radical chosen from the group comprising H, methyl, butyl, pentyl, benzyl, p-methoxybenzyl, 2-pyridinylmethyl, 3-pyridinylmethyl and/or imidazolylmethyl and the structural element $X^3$ is H.

One advantage of these embodiments is that they can have a particularly good affinity for the κ receptor. For example, the $K_i$ value, as a measure of the affinity for the κ receptor, can be in the range of from $\geq 0.01$ nM to $\leq 50$ nM, preferably in the range of from $\geq 0.5$ nM to $\leq 20$ nM, preferably in the range of from $\geq 1$ nM to $\leq 10$ nM.

In further preferred embodiments, the structural element $R^1$ is H.

Compounds and/or racemates, enantiomers, diastereomers, solvates, hydrates thereof and pharmaceutically acceptable salts and/or esters thereof which are preferred in particular have the following general formula (4):

(4)

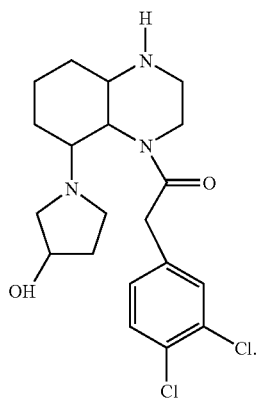

(4b)

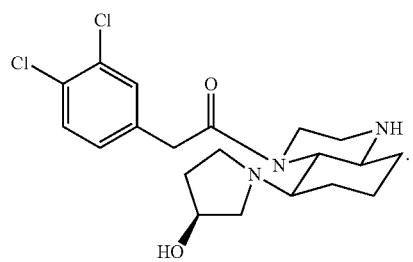

Compounds of the formula (4) can provide the advantage of a particularly good analgesic action, in particular peripheral analgesic action.

The compounds according to the invention of the formula (1), in particular the compounds of the formula (4), can be in the form of the racemates, diastereomers or enantiomer pairs. The racemates, diastereomers or enantiomers of each pair can be separated by conventional methods, preferably by means of high performance liquid chromatography (HPLC).

In preferred embodiments, the compound (1) includes a mixture comprising enantiomers according to the following formulae (1a) and/or (1b):

(1a)

(1b)

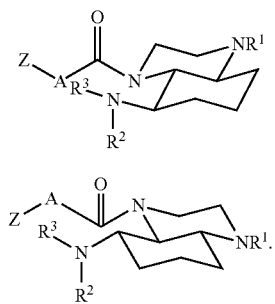

Preferably, the enantiomers (1a) and (1b) of the compound (1) are in the form of a racemate.

It may be preferable for the compounds according to the invention to be in the form of an enantiomer chosen from the formulae (1a) and/or (1b).

In preferred embodiments, the compound (4) can contain the following diastereomers according to the following formulae (4a) and/or (4b).

(4a)

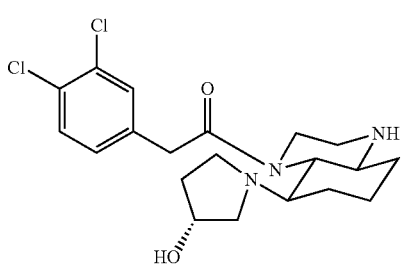

It goes without saying that, unless expressly stated otherwise, if the structure of only one stereoisomer, in particular enantiomer, is shown in the context of the present invention, in each case the other stereoisomer(s), in particular enantiomers, are included.

Further preferred compounds and/or racemates, enantiomers, diastereomers, solvates, hydrates thereof and pharmaceutically acceptable salts and/or esters thereof have the following formula (6):

(6)

It has been found that compounds of the formula (6) can provide a particularly good analgesic action, in particular peripheral analgesic action.

The compounds according to the invention can be used in the form of their racemates, their pure stereoisomers, in particular enantiomers or diastereomers, or in the form of mixtures of the stereoisomers, in particular the enantiomers or diastereomers.

Preferred compounds are chosen from the group comprising 2-(3,4-dichlorophenyl)-1-[(4aRS,8SR,8aRS)-8-(pyrrolidin-1-yl)-perhydroquinoxalin-1-yl]-ethan-1-one, and/or the diastereomers 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one and a diastereomer mixture thereof.

Further preferred compounds are chosen from the group comprising 1-[(4aRS,8SR,8aRS)-4-benzoyl-8-(pyrrolidin-1-yl)-perhydroquinoxalin-1-yl]-2-(3,4-dichlorophenyl) ethan-1-one, 1-[(4aRS,8SR,8aRS)-4-acetyl-8-(pyrrolidin-1-yl)-perhydroquinoxalin-1-yl]-2-(3,4-dichlorophenyl)ethan-1-one, 1-{(4aRS,8SR,8aRS)-1-[2-(3,4-dichlorophenyl) acetyl]-8-(pyrrolidin-1-yl)-perhydroquinoxalin-4-yl}propan-1-one, methyl{(4aRS,8SR,8aRS)-1-[2-(3,4-dichlorophenyl)acetyl]-8-(pyrrolidin-1-yl)- perhydroquinoxalin-4-yl}carboxylate, ethyl{(4aRS,8SR, 8aRS)-1-[2-(3,4-dichlorophenyl)acetyl]-8-(pyrrolidin-1-yl)-perhydroquinoxalin-4-yl}carboxylate, 3-{(4aRS,8SR, 8aRS)-1-[2-(3,4-dichlorophenyl)acetyl]-8-(pyrrolidin-1-yl)-perhydroquinoxalin-4-yl}-3-oxopropionic acid, 4-{(4aRS, 8SR,8aRS)-1-[2-(3,4-dichlorophenyl)acetyl]-8-(pyrrolidin-1-yl)perhydroquinoxalin-4-yl}-4-oxobutyric acid, methyl 3-{(4aRS,8SR,8aRS)-1-[2-(3,4-dichlorophenyl)acetyl]-8-(pyrrolidin-1-yl)-perhydroquinoxalin-4-yl}-3-oxopropionate, 1-{(4aRS,8SR,8aRS)-4-benzoyl-8-[(3SR)- and (3RS)-3-hydroxypyrrolidin-1-yl]-perhydroquinoxalin-1-yl}-2-(3,4-dichlorophenyl)ethan-1-one, methyl{(4aRS,8SR, 8aRS)-1-[2-(3,4-dichlorophenyl)acetyl]-8-[(3SR)- and (3RS)-3-hydroxypyrrolidin-1-yl]-perhydroquinoxalin-4-yl}carboxylate, 3-{(4aRS,8SR,8aRS)-1-[2-(3,4-dichlorophenyl)acetyl]-8-[(3SR)- and (3RS)-3-hydroxypyrrolidin-1-yl]-perhydroquinoxalin-4-yl}-3-oxopropionic acid, methyl 3-{(4aRS,8SR,8aRS)-1-[2-(3,4-dichlorophenyl) acetyl]-8-[(3SR)- and (3RS)-3-hydroxypyrrolidin-1-yl]-perhydroquinoxalin-4-yl}-3-oxopropionate, 2-(3,4-dichlorophenyl)-1-[(4aRS,8SR,8aRS)-4-methyl-8-(pyrrolidin-1-yl)-perhydroquinoxalin-1-yl]ethan-1-one, 1-[(4aRS,8SR, 8aRS)-4-butyl-8-(pyrrolidin-1-yl)perhydroquinoxalin-1-yl]-2-(3,4-dichlorophenyl)-ethan-1-one, 1-[(4aRS,8SR,8aRS)-4-benzyl-8-(pyrrolidin-1-yl)perhydroquinoxalin-1-yl]-2-(3, 4-dichlorophenyl)ethan-1-one, 2-(3,4-dichlorophenyl)-1-[(4aRS,8SR,8aRS)-4-(4-methoxybenzyl)-8-(pyrrolidin-1-yl)-perhydroquinoxalin-1-yl]ethan-1-one, 2-(3,4-dichlorophenyl)-1-{(4aRS,8SR,8aRS)-4-[(pyridin-2-yl) methyl]-8-(pyrrolidin-1-yl)perhydroquinoxalin-1-yl}ethan-1-one, 2-(3,4-dichlorophenyl)-1-{(4aRS,8SR,8aRS)-4-[(pyridin-3-yl)methyl]-8-(pyrrolidin-1-yl) perhydroquinoxalin-1-yl}ethan-1-one, 2-(3,4-dichlorophenyl)-1-{(4aRS,8SR,8aRS)-4-[(1H-imidazol-5-yl)methyl]-8-(pyrrolidin-1-yl)perhydroquinoxalin-1-yl}ethan-1-one, 2-(3,4-dichlorophenyl)-1-{(4aRS,8SR, 8aRS)-4-methyl-8-[(3SR)- and (3RS)-3-hydroxypyrrolidin-1-yl]-perhydroquinoxalin-1-yl}ethan-1-one, 1-{(4aRS,8SR, 8aSR)-4-benzyl-8-[(3SR)- and (3RS)-3-hydroxypyrrolidin-1-yl]perhydroquinoxalin-1-yl}-2-(3,4-dichlorophenyl) ethan-1-one and/or 2-(3,4-dichlorophenyl)-1-{(4aRS,8SR, 8aSR)-4-[(pyridin-3-yl)methyl]-8-[(3SR)- and (3RS)-3-hydroxypyrrolidin-1-yl]perhydroquinoxalin-1-yl}ethan-1-one.

The compounds according to the invention can furthermore be used in the form of their acids or their bases or in the form of their salts or esters, in particular the physiologically acceptable salts or esters, or in the form of their solvates, in particular the hydrates.

In particular, pharmaceutically acceptable addition salts of the compounds according to the invention can advantageously be used.

The pharmaceutically acceptable salts can be base addition salts. These include salts of the compounds according to the invention with inorganic bases, such as alkali metal hydroxides, alkaline earth metal hydroxides, or with organic bases, such as mono-, di- or triethanolamine.

Acid addition salts, in particular with inorganic acids, such as hydrochloric acid, sulfuric acid or phosphoric acid, or with suitable organic carboxylic or sulfonic acids, or with amino acids, can further advantageously be used.

In preferred embodiments, pharmaceutically acceptable salts include non-toxic addition salts of the compounds according to the invention, for example in the form of the free base, with organic or inorganic acids. Examples of inorganic acids include HCl, HBr, sulfuric acid and phosphoric acid. Organic acids are preferably chosen from the group comprising acetic acid, propionic acid, pyruvic acid, butyric acid, alpha-, beta- or gamma-hydroxybutyric acid, valeric acid, hydroxyvaleric acid, caproic acid, hydroxycaproic acid, caprylic acid, capric acid, lauric acid, myristic acid, palmitic acid, stearic acid, glycolic acid, lactic acid, D-glucuronic acid, L-glucuronic acid, D-galacturonic acid, glycine, benzoic acid, hydroxybenzoic acid, gallic acid, salicylic acid, vanillic acid, coumaric acid, caffeic acid, hippuric acid, orotic acid, L-tartaric acid, D-tartaric acid, D,L-tartaric acid, mesotartaric acid, fumaric acid, L-malic acid, D-malic acid, D,L-malic acid, oxalic acid, malonic acid, succinic acid, maleic acid, oxaloacetic acid, glutaric acid, hydroxyglutaric acid, ketoglutaric acid, adipic acid, ketoadipic acid, pimelic acid, glutamic acid, aspartic acid, phthalic acid, propanetricarboxylic acid, citric acid, isocitric acid, methanesulfonic acid, toluenesulfonic acid, benzenesulfonic acid, camphorsulfonic acid, embonic acid and/or trifluoromethanesulfonic acid.

Pharmaceutically acceptable salts of the compounds according to the invention are chosen, for example, from the group comprising chlorides, bromides, iodides, hydrochlorides, hydrobromides, sulfonates, methanesulfonates, sulfates, hydrogen sulfates, sulfites, hydrogen sulfites, phosphates, nitrates, methanoates, acetates, prioionates, lactates, citrates, glutarates, maleates, malonates, malates, succinates, tartrates, oxalates, fumarates, benzoates, p-toluenesulfonates and/or salts of amino acids, preferably the proteinogenic amino acids.

Pharmaceutically acceptable esters of the compounds which can be used are, in particular, physiologically readily hydrolyzable esters, for example chosen from the group comprising alkyl, pivaloyloxymethyl, acetoxymethyl, phthalidyl, indanyl and/or methoxymethylene esters.

In embodiments which are furthermore preferred, the compounds according to the invention can be derivatized, for example phosphorylated, glycosylated, acetylated, ubiquitinylated, farnesylated, palmitoylated, geranylgeranylated and/or biotinylated.

The structural element $R^1$ is particularly preferably derivatized. In particularly preferred embodiments, the structural element $R^1$ is biotinylated.

Without being tied to a particular theory, it is assumed that the compounds according to the invention are capable of having an analgesic, antipyretic, antiphlogistic, antipruritic and/or spasmolytic action.

In preferred embodiments, one advantage of the compounds is that these compounds pass the blood-brain barrier to only a small extent. This makes it possible for the compounds according to the invention to be usable in particular as peripherally acting analgesics.

On the basis of their advantageous properties, the compounds according to the invention are suitable for use as medicaments.

The compounds according to the invention are preferably toxicologically acceptable and are therefore suitable as pharmaceutically active compounds and/or medicaments.

The invention also provides the use of the compounds according to the invention, in particular of the compounds of the formulae (4) and (6), for the preparation of a medicament.

In advantageous embodiments the compounds according to the invention can be used in particular for therapeutic and/or prophylactic treatment, diagnosis and/or therapy of diseases chosen from the group comprising pain-related diseases, inflammatory diseases and/or gastrointestinal diseases.

The compounds according to the invention can have a positive influence in particular on peripheral pain. In particular, it has been found, surprisingly, that preferred embodiments of the compounds according to the invention have an analgesic activity.

For example, it has been found experimentally in an in vivo model that the compounds of the formulae (4) and (6) have an analgesic activity. The compound of the formula (6) showed an even better analgesic action here than the compound of the formula (4).

The invention also provides the use of the compounds according to the invention, in particular of the compounds of the formulae (4) and (6), for the preparation of a medicament for therapeutic and/or prophylactic treatment of diseases chosen from the group comprising pain-related diseases, inflammatory diseases and/or gastrointestinal diseases.

The compounds according to the invention can be used by themselves or in combination with known substances for treatment of diseases chosen from the group comprising pain-related diseases, inflammatory diseases and/or gastrointestinal diseases.

Pain-related diseases include acute and chronic pain.

Pain-related diseases can be chosen in particular from the group comprising back pain, facial pain, headaches, joint pain, muscular pain syndromes, inflammatory pain-related diseases, neuropathic pain, peripheral pain, peripheral nerve damage, visceral pain, abdominal pain, menstruation symptoms, kidney- and gallstone pain, itching, cancer and tumor pain, sympathetic pain, postoperative pain, post-traumatic pain, hyperalgesia and/or inflammatory pain.

Facial pain is preferably chosen from the group comprising trigeminal neuralgia, toothache, earache, craniomandibular dysfunction and/or chronic idiopathic facial pain.

Headaches are preferably chosen from pain in the head organs, such as cranium, meninges, blood vessels in the brain, cranial nerves and uppermost spinal nerves. Preferred forms of headache are chosen from the group of migraine headache, stress headache, cluster headache (Horton's syndrome) and substance-induced headaches, for example due to intake of medicaments.

Back pain is preferably chosen from the group comprising vertebral column syndrome of the cervical, thoracic or lumbar vertebral column, pain in the coccyx and/or ischial pain.

Inflammatory pain-related diseases are preferably chosen from the group comprising polyarthritis and/or rheumatoid arthritis.

Peripheral nerve damage is preferably chosen from the group comprising stump and phantom pain, neuropathic pain, polyneuropathy, post-zoster neuralgia and/or intercostal neuralgia.

Abdominal pain preferably includes irritable bowel syndrome (IBS).

Menstruation symptoms include pain and cramps.

Hyperalgesia is understood as meaning the increased sensation of a pain stimulus.

In the treatment in particular of chronic peripheral pain in humans, an advantageous effect on the course of the disease can be achieved by using the compounds according to the invention. A further advantage of the compounds according to the invention can result from the fact that no or only mildly centrally mediated side effects, such as respiratory depression, vomiting, bradycardia or constipation, can occur.

In particular, in preferred embodiments the compounds according to the invention are suitable as peripheral analgesics.

It is of particular advantage that the compounds according to the invention preferably show no euphoric action. This can provide the advantage that administration of the compounds according to the invention lead to relatively mild or no psycho-dependency. This makes it possible to be able to administer the compounds according to the invention over a relatively long period of time. For example, a long-term administration, in particular a daily administration, is made possible. This makes possible, for example, administration for treatment of pain-related diseases for which under certain circumstances therapy must be continued for months or years.

The compounds according to the invention are preferably suitable for treatment of chronic pain.

Studies have shown, for example in the "writhing test" on mice, that the compounds according to the invention can have an analgesic activity, as described in Example 28. The investigations were performed on mice, as described by L. C. Hendershot, J. Forsaith, J. Pharmacol. Exp. Ther. 125,237-240 (1959), to which reference is herewith made in its full scope.

The compounds according to the invention can furthermore be suitable as a local anesthetic. For example, the compounds according to the invention can be suitable for alleviating the pain of insect bites, such as mosquito bites, or burns. In particular, the compounds according to the invention can be suitable for alleviating the pain of painful insect bites or stings, such as wasp or bee stings.

The compounds according to the invention can furthermore be used for treatment of pain stimuli, such as itching.

The compounds according to the invention, in particular the compounds of the formula (4) and (6), can provide the advantage, in particular, of being suitable for treatment of itching.

Itching, also called pruritus, is a frequent symptom in skin therapy and also represents a major problem in other specialist medical fields. Itching is conventionally experienced as a type of pain stimulus. The itching sensation triggers the desire to scratch the affected area. However, scratching intensifies the itching. Skin damaged by scratching further offers infectious pathogens a good nutrient medium and inflammations of scratched-open areas of skin are not infrequent. Thus, for example, dialysis patients often suffer from itching and its secondary damage. Chronic itching in particular is often difficult to treat and is a severe physical and mental burden.

The invention therefore particularly preferably provides the use of the compounds according to the invention for the preparation of a medicament for therapeutic and/or prophylactic treatment of itching.

In particular, preventive administration of the compounds according to the invention can be advantageous if itching is expected, for example after dialysis.

The compounds according to the invention or compositions containing these can be administered systemically or topically. Preferably, the compounds or compositions according to the invention are administered topically, in particular in the form of creams, ointments, plasters or tinctures.

Inflammatory diseases can be chosen in particular from the group comprising inflammatory diseases of the gastrointestinal tract, inflammatory intestinal diseases, such as Crohn's disease and/or colitis ulcerosa, acute or chronic inflammatory changes with inflammation of the gall bladder, inflammatory pseudopolyps, colitis cystica profunda, pneumatosis cystoides intestinales, pancreatitis, appendicitis, inflammatory diseases of the joints, such as rheumatoid arthritis, and/or inflammatory diseases of the skin and of the eyes.

Use of the compounds according to the invention is suitable in particular in cases of chronic inflammatory intestinal diseases, such as Crohn's disease or colitis ulcerosa.

A particular advantage of the compounds according to the invention can be provided by these being usable in particular for treatment and/or prophylaxis of inflammatory gastrointestinal diseases.

Gastrointestinal diseases can be chosen in particular from the group comprising irritable bowel syndrome, gastric lesions, gastrointestinal ulcerations, exogenous and endogenous damage to the gastrointestinal mucosa, malfunctions of the gastrointestinal tract, adenomas, in particular in the intestine, and/or juvenile polyps.

In the context of this invention, malfunctions of the gastrointestinal tract also include passage dysfunctions and colic, such as biliary colic.

The compounds according to the invention can furthermore be particularly suitable for use for treatment of inflammatory gastrointestinal diseases. For example, in addition to the analgesic and anti-inflammatory action, the compounds according to the invention can be suitable for normalizing disturbances in intestinal motor function and/or malfunctions of the gastrointestinal tract caused by the disease.

For example, irritable bowel syndromes are the most frequent cause of abdominal pain syndromes. An advantage of the compounds according to the invention can be provided in that the compounds according to the invention are able to alleviate the pain associated with irritable bowel syndrome and/or to cure the disease. It is of particular advantage that the compounds according to the invention preferably show no adverse effects on normal intestinal peristalsis.

Preferred indications are chosen from the group comprising pain conditions, inflammations, hyperalgesia, neuropathic pain, visceral pain, peripheral pain, inflammatory pain, rheumatoid arthritis, menstruation symptoms comprising pain and/or cramps, kidney- and gallstone pain, postoperative pain, pruritus, gastrointestinal symptoms, such as irritable bowel syndrome, and/or inflammatory intestinal diseases, such as Crohn's disease and colitis ulcerosa.

The invention also provides medicaments comprising at least one compound according to the invention and/or racemates, enantiomers, diastereomers, solvates, hydrates thereof and pharmaceutically acceptable salts and/or esters thereof. Medicaments comprising compounds of the formulae (4) or (6) and/or racemates, enantiomers, diastereomers, solvates, hydrates thereof and pharmaceutically acceptable salts and/or esters thereof are preferred. The medicaments according to the invention can furthermore also contain mixtures of two or more of the compounds according to the invention.

Preferred medicaments are analgesics. Medicaments for treatment of chronic pain are particularly preferred.

Medicaments which are preferred in particular are furthermore medicaments for treatment of itching, in particular chronic itching.

A preferred use of the medicaments comprising compounds according to the invention comprises therapeutic and/or prophylactic treatment of diseases chosen from the group comprising pain-related diseases, inflammatory diseases and/or gastrointestinal diseases. The medicaments according to the invention are preferably suitable for treatment of pain. The medicaments according to the invention are further preferably suitable for treatment of itching.

In the context of the present invention, the term "prophylactic treatment" is understood as meaning in particular that the compounds according to the invention can be administered prophylactically, before symptoms of a disease occur or the risk of a disease exists. In particular, a "prophylactic treatment" is understood as meaning prevention by medicaments.

Medicaments which are further preferred comprise at least one compound according to the invention and/or racemates, enantiomers, diastereomers, solvates, hydrates thereof and pharmaceutically acceptable salts and/or esters thereof and at least one opioid receptor antagonist, preferably chosen from the group comprising naloxone, naltrexone, cyprodime, naltrindole, norbinaltorphimine nalmefene, nalorphine, nalbuphine, naloxonazine, methylnaltrexone and/or ketylcyclazocine, preferably chosen from the group comprising naloxone, naltrexone, cyprodime, naltrindole and/or norbinaltorphimine. The use of a medicament comprising at least one compound according to the invention and/or racemates, enantiomers, diastereomers, solvates, hydrates thereof and pharmaceutically acceptable salts and/or esters thereof and at least one opioid receptor antagonist, preferably chosen from the group comprising naloxone, naltrexone, cyprodime, naltrindole, norbinaltorphimine nalmefene, nalorphine, nalbuphine, naloxonazine, methylnaltrexone and/or ketylcyclazocine is further preferred. The use of a medicament comprising at least one compound according to the invention and/or racemates, enantiomers, diastereomers, solvates, hydrates thereof and pharmaceutically acceptable salts and/or esters thereof and at least one opioid receptor antagonist, preferably chosen from the group comprising naloxone, naltrexone, cyprodime, naltrindole, norbinaltorphimine nalmefene, nalorphine, nalbuphine, naloxonazine, methylnaltrexone and/or ketylcyclazocine for therapeutic and/or prophylactic treatment of diseases chosen from the group comprising pain-related diseases, inflammatory diseases and/or gastrointestinal diseases, in particular itching, is preferred in particular.

The compounds according to the invention can be administered according to conventional methods, for example orally, dermally, intranasally, transmucosally, pulmonally, enterally, buccally, rectally, by inhalation, by means of injection, for example intravenously, parenterally, intraperitoneally, intradermally, subcutaneously and/or intramuscularly and/or locally, for example on painful areas of the body. Oral administration is particularly preferred.

The compounds according to the invention and/or racemates, enantiomers, diastereomers, solvates, hydrates thereof and pharmaceutically acceptable salts and/or esters thereof can be used in particular for the preparation of medicaments by being brought into a suitable dosage form together with at least one carrier substance or auxiliary substance.

Medicaments can be in the form of and/or administered as liquid, semi-solid or solid drug forms, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules.

Formulations in the form of tablets, coated tablets, capsules, granules, pellets, drops, juices and syrups are preferably suitable for oral administration.

Solutions, preferably oily or aqueous solutions, suspensions, emulsions, implants and sprays are preferably suitable for parenteral, topical or inhalatory administration. The compounds according to the invention can also be usable as easily reconstitutable dry formulations, for example lyophilized, the lyophilisates obtained being usable, for example, for the preparation of injection preparations.

Formulations which are suitable for percutaneous administration can be included, for example, in a depot in dissolved form or in a plaster, optionally with the addition of agents which promote penetration through the skin. Formulation forms which can be used orally or percutaneously can also release the corresponding compounds in a delayed manner.

Pharmaceutical dosage forms with delayed release (sustained release formulation) are furthermore preferred for oral administration of the compounds according to the invention. Formulations which are resistant to gastric juice may be preferred. Examples of formulations with delayed release are sustained release matrix tables, multilayered tablets, the coating of which can be, for example, constructed to be resistant to gastric juice, such as coatings based on shellac, sustained release capsules or formulations using biodegradable polymers, for example poly(lactic acid) polymers.

The compounds according to the invention can be formulated for intravenous administration. Sterile suspensions for parenteral administration, in particular for intravenous injection, are preferred. Auxiliary substances and/or solvents which are suitable in particular for injection solutions are preferably chosen from the group comprising dimethylsulfoxide (DMSO), alcohols, preferably polyfunctional alcohols, preferably chosen from the group comprising glycerol and/or propylene glycol, and/or plant oils.

Compositions for topical use can be in the form, for example, of pharmaceutically acceptable powers, lotions, ointments, creams, gels or of therapeutic systems, which contain therapeutically active amounts of the compounds according to the invention. The compounds according to the invention can be administered as individual therapeutic active compounds or as mixtures with other therapeutic active compounds. They can be administered by themselves, and they are preferably administered in the form of medicaments, in particular as mixtures with suitable pharmaceutical carriers.

Conventional physiologically acceptable pharmaceutical auxiliary substances, preferably chosen from the group comprising carrier materials, fillers, solvents, diluents, wetting agents, emulsifiers, dyestuffs, preservatives, disintegrating agents, lubricants, salts for influencing the osmotic pressure, buffer substances, aromas and/or binders, can be used for the preparation of the medicaments.

Carrier substances which can be used are organic or inorganic substances which are suitable for enteral, for example oral or rectal, or parenteral administration and do not react with the compounds, for example water, plant oils, benzyl alcohols, polyethylene glycols, glycerol triacetate and other fatty acid glycerides, gelatin, soya lecithin, carbohydrates, such as lactose or starch, magnesium stearate, talc or cellulose.

The medicaments mentioned can be sterilized.

The compounds can be prepared by conventional synthesis methods.

The compounds according to the invention can particularly preferably be prepared by a process for the preparation of the compounds according to the invention comprising the following steps:
a) cyclization of nitromethane and glutaraldehye to give 2-nitrocyclohexane-1,3-diol;
b) amination of the nitrodiol obtained in step a) with primary or secondary amines;
c) reduction of the nitro group of the nitrodiamine to give a primary amine;
d) reaction of the cyclohexanetriamine obtained in step c) with dialkyl oxalate;
e) splitting off of an amine radical of the compound obtained in step d);
f) alkylation of the compound obtained in step e), with introduction of the groups $R^2$ and $R^3$;
g) reduction of the perhydroquinoxalinedione ring of the compound obtained in step f) to give the perhydroquinoxaline;
h) acylation of the secondary amine obtained in step g), with introduction of a group C(O)-A-Z;
i) introduction of a radical $R^1$, preferably by alkylation, acylation or hydrogenolytic introduction of H.

For the groups A, Z, $R^1$, $R^2$ and $R^3$, reference is made to the above description in its full scope.

The cyclization of nitromethane and glutaraldehyde to give 2-nitrocyclohexane-1,3-diol according to step a) of the process according to the invention is preferably carried out under base catalysis, preferably using sodium hydroxide solution as the base. Preferably, the reaction is carried out in a protic solvent, preferably in methanol.

For the amination of the nitrodiol obtained in step a), primary amines can preferably be used, preferably chosen from the group comprising pyrrolidine, benzylamine, p-methoxybenzylamine, p-chlorobenzylamine and/or 3,4-dichlorobenzylamine. Benzylamine can preferably be used. Preferably, the reaction is carried out in a protic solvent, preferably in water.

In preferred embodiments, the reduction of the nitro group of the nitrodiamine to a primary amine in step c) of the process according to the invention is carried out with methanol over Raney nickel or with hydrogen in the presence of the Raney nickel catalyst. Freshly activated Raney nickel can preferably be used. Hydrogen gas is preferably fed to the reaction. A preferred pressure of the hydrogen is in the range of from 0.2 bar to 100 bar, preferably in the range of from 0.5 bar to 8 bar, particularly preferably 1 bar.

The reduction can be carried out in an aprotic solvent. Preferably, the reduction is carried out in a protic solvent. The reduction is preferably carried out in a solvent chosen from the group comprising methanol, ethyl acetate, water and/or tetrahydrofuran, preferably in methanol. Preferred reaction temperatures are in a range of from 20° C. to 40° C.

The reaction of the cyclohexanetriamine obtained in step c) with dialkyl oxalate is preferably carried out in a solvent chosen from the group comprising methanol and/or ethyl acetate. Dimethyl and diethyl oxalate can preferably be used, and dimethyl oxalate can particularly preferably be used. A ring closure to give a perhydroquinoxalinedione derivative can be carried out by this reaction of the cyclohexanetriamine with dialkyl oxalate.

The amine radicals present due to the amination of the nitrodiol obtained in step a) with primary or secondary amines are split off in step e). A compound which is preferably used for the amination is benzylamine, and debenzylation of the benzylamine substituents therefore preferably takes place. A debenzylation is preferably carried out with hydrogen under 1 bar using palladium-on-active charcoal as the catalyst. Hydrogen can also be obtained in situ from chemical sources of hydrogen, such as ammonium formate, hydrazine or formic acid. Splitting off of the benzyl radical is preferably carried out by catalytic transfer hydrogenolysis with ammonium format and palladium-on-active charcoal. The reaction is preferably carried out under reflux. A preferred solvent is methanol. Production of a primary amine is preferably carried out.

In a further step f), an alkylation of the compound obtained in step e), with introduction of the groups $R^2$ and $R^3$ is carried out. A reductive alkylation of a primary amine is preferred. For example, a reaction with formalin and sodium cyanoborohydride ($NaBH_3CN$) in a protic solvent, preferably in methanol, can be carried out.

An alkylation of the amine with haloalkanes is preferably carried out. A reaction with iodo- or bromoalkanes and $NaHCO_3$ in acetonitrile under reflux is preferably carried out.

Iodoalkanes are preferred, preferably chosen from the group comprising iodomethane, iodoethane, 1,4-diiodobutane, 1,5-diiodopentane. Bromoalkanes are also preferred, in particular 1,4-dibromobutan-2-ol. Iodomethane or iodoethane can preferably be used.

Terminally halogenated dihaloalkanes can preferably be used for formation of a nitrogen-containing ring. Dihaloalkanes containing two to six C atoms are particularly preferred. These can be mono- or disubstituted by OH and/or carbonyl groups. The dihaloalkanes having four C atoms are very particularly preferred. The dihaloalkanes are preferably chosen from the group comprising 1,4-diiodobutane, 1,4-dibromobutan-2-ol and/or 1,5-diiodopentane.

The alkylation can be carried out using auxiliary bases. Preferred auxiliary bases are chosen from the group comprising potassium carbonate, sodium carbonate, potassium bicarbonate and/or sodium bicarbonate. The alkylation can be carried out in an aprotic solvent. Preferably, the alkylation is carried out in a protic solvent. Solvents which can be used are preferably chosen from the group comprising acetone, acetonitrile and/or methanol, in particular acetonitrile.

The reduction of the perhydroquinoxalinedione ring of the compound obtained in step f) to give the perhydroquinoxaline is preferably carried out using the reducing agent lithium aluminum hydride (LiAlH$_4$). A combination with Lewis acids, for example aluminum chloride, is further preferred. A 3:1 mixture of lithium aluminum hydride (LiAlH$_4$) and aluminum chloride is preferred. The reduction can be carried out in an aprotic solvent. Preferably, the reduction is carried out in a protic solvent. A preferred solvent is tetrahydrofuran (THF). The reduction is preferably carried out under a nitrogen inert gas atmosphere.

In a further step, an acylation of the secondary amine obtained in step g), with introduction of a group C(O)-A-Z, is carried out.

The acylation can be carried out with acylating agents, such as acid chlorides or analogous free carboxylic acids. The acylation is preferably carried out with acid chlorides. Phenylacetyl chloride derivatives can particularly preferably be used. 2-(3,4-Dichlorophenyl)acetyl chloride and 2-phenylacetyl chloride are particularly preferred. The acylation with carboxylic acids is preferably carried out with catalysts. These are particularly preferably chosen from the group comprising dicyclohexylcarbodiimide (DCC) and N'-(3-dimethylaminopropyl)-N-ethylcarbodiimide (EDC).

The acylation of hydroxypyrrolidine derivatives with acylating agents is preferably carried out in the ratio of 1:1.

In a further process step, an introduction of a radical $R^1$, preferably by alkylation, acylation or hydrogenolytic introduction of H, is carried out.

In preferred embodiments, a radical present can be split off hydrogenolytically, as a result of which a hydrogenolytic introduction of H as the radical $R^1$ takes place. Further radicals $R^1$ can then be introduced in a step.

For a hydrogenolytic cleavage, elemental hydrogen is preferably employed, with palladium-on-carbon as the catalyst. Hydrochloric acid is preferably added to the mixture. The hydrogenolytic cleavage can be carried out in an aprotic solvent. Preferably, the hydrogenolytic cleavage is carried out in a protic solvent. Preferred solvents are chosen from the group comprising water and/or tetrahydrofuran (THF). 1:1 mixtures of water and tetrahydrofuran are preferred. A preferred pressure of the hydrogen is in the range of from 0.5 bar to 8 bar, preferably 1 bar.

The radical $R^1$ can particularly preferably be introduced by alkylation or acylation of the secondary amine.

An alkylation with aldehydes is preferably carried out as a reductive alkylation. Sodium cyanoborohydride or sodium triacetoxyborohydride are preferably used as the catalyst. Aldehydes are particularly preferably chosen from the group comprising formaldehyde, butyraldehyde, anisaldehyde, pyridine-2-carbaldeyde, nicotinaldehyde and/or 1H-imidazole-5-carbaldehyde.

An acylation is preferably carried out with acylating agents such as acid chlorides or analogous free carboxylic acids. The acylation with acid chlorides is particularly preferred. Acid chlorides chosen from the group comprising benzoyl chloride, acetyl chloride, propionyl chloride, methyl chloroformate, ethyl chloroformate, malonic acid monomethyl ester chloride and/or succinic anhydride are very particularly preferred.

Esterified radicals can be converted into free acids by ester cleavage.

The reactions which can be carried out under reflux can also be carried out in a synthesis microwave oven.

By the reaction of the cyclohexanetriamine with dimethyl oxalate to give a quinoxaline derivative in step d) of the process according to the invention, a racemate comprising two enantiomers is formed.

In preferred embodiments of the process, separation of racemates is therefore envisaged. In further preferred embodiments of the process, separation of diastereomer mixture can be envisaged.

The separation of the racemates, diastereomers or enantiomers can be carried out by known methods, in particular chromatography methods, preferably by means of high performance liquid chromatography (HPLC) or column chromatography or flash chromatography (FC).

A separation of racemates, diastereomers or enantiomers is preferably carried out by means of chiral chromatography methods, in particular chiral high performance liquid chromatography. Chiral column material is commercially obtainable.

The separation of a racemate can also be carried out by reaction of a racemic mixture of an organic acid with a pure enantiomer of an acid. The diastereomeric salts formed can be separated by fractional crystallization. The splitting of the racemate is preferably carried out by reacting the racemate with an enantiomerically pure acid. The separation is then carried out by fractional recrystallization or chromatography methods, it being possible for the methods to be combined and carried out several times.

In the context of the present invention, the stated sequence of process steps a) to i) is not to be understood in the sense of a fixed sequence. Depending on the process chosen, the sequence of process steps can vary accordingly. It is preferable for the process steps to be carried out in the stated sequence.

In preferred embodiments, the compounds obtained can be purified, for example by means of chromatography methods, preferably, for example, by means of high performance liquid chromatography or column chromatography.

Examples which serve to illustrate the present invention are given in the following.

Round-bottomed flasks were used for the chemical reactions. If substances sensitive to hydrolysis and/or oxidation were used or if hydrogenations were carried out with elemental hydrogen, dry Schlenk flasks were employed. Nitrogen from Air Liquide, Düsseldorf was employed as the inert gas. When working with inert gas, substances were added either in counter-current or through septa.

Reactions at 0° C. were cooled by an ice/water mixture. The course of the reaction and the associated completeness of a reaction was monitored by thin layer chromatography.

Substances isolated were stored at +5° C.

The solvents employed were obtained in p.A. quality (p.A., for analysis) and used without further purification. Anhydrous, absolute solvents were prepared by distillation over a desiccant in an inert gas atmosphere. Water was employed in demineralized form.

Purification of the compounds was carried out by means of flash chromatography, a variant of column chromatography. Silica gel 60 (40-63 μm) from Merck was used as the stationary phase. The mobile phase, the column diameter (Ø), the silica gel packing height and the fraction volume were adapted to the conditions of the experiment and are described in the individual preparation instructions.

Example 1

Preparation of 2-(3,4-dichlorophenyl)-1-[(4aRS,8SR, 8aRS)-8-(pyrrolidin-1-yl)-perhydroquinoxalin-1-yl]-ethan-1-one 1.1 Preparation of (2r)-2-nitrocyclohexane-1,3-diol A 25% strength aqueous glutaraldehyde solution (182 ml, 460 mmol), nitromethane (38 ml, 0.71 mol) and $CH_3OH$ (600 ml) were introduced into a 1 l round-bottomed flask. 2 M NaOH (12 ml) was added dropwise at 0 to 5° C. The ice-bath was removed and the mixture was stirred at room temperature (20-23° C.) for 4 hours. The yellow solution formed was neutralized by addition of acid cation exchanger (Merck) (16.8 g) and the mixture was stirred for 20 minutes. The exchanger resin was filtered off and washed with a little $CH_3OH$. The filtrate was evaporated to a semi-solid state in vacuo. The residue was taken up in EtOH (100 ml) and toluene (250 ml). The two-phase mixture formed was evaporated again in vacuo. The solid formed was dissolved in hot (65° C. to 70° C.) EtOH (100 ml) and toluene (250 ml) was added. The colorless crystals formed were filtered off and dried under a high vacuum.

1.2 Preparation of (2r)-$N^1,N^3$-dibenzyl-2-nitrocyclohexane-1,3-diamine

Benzylamine (26.4 ml, 0.24 mol) was dissolved in $H_2O$ (60 ml) in a 250 ml round-bottomed flask and (2r)-2-nitrocyclohexane-1,3-diol (19.3 g, 0.12 mol) was added. The yellow solution was stirred at room temperature for 16 hours. The yellow precipitate formed was filtered off and then recrystallized with $CH_3OH$. A colorless solid was obtained.

1.3 Preparation of (2r)-$N^1,N^3$-dibenzylcyclohexane-1,2,3-triamine (2r)-$N^1,N^3$-Dibenzyl-2-nitrocyclohexane-1,3-diamine (0.34 g, 1.0 mmol) was dissolved in $CH_3OH$ (2.5 ml) and Raney nickel (Acros Organics, Geel, Belgium) was added (0.96 g; 1 ml of settled suspension contained about 0.6 g of Raney nickel; cf. Gattermann, L; Wieland, H.; Wieland, T.; Sucrow, W. Die Praxis des organischen Chemikers, $43^{rd}$ edition; Walter de Gryter: Berlin 1982; 555). The suspension was stirred under 1 bar of $H_2$ at room temperature for 3 hours. The catalyst was then filtered off and the solution was evaporated in vacuo. A pale yellow oil was obtained.

1.4 Preparation of (4aRS,5SR,8aRS)-1-benzyl-5-(benzylamino)perhydroquinoxaline-2,3-dione (2r)-$N^1,N^3$-Dibenzylcyclohexane-1,2,3-triamine (100 mg, 0.32 mmol) was dissolved in $CH_3OH$ (2.0 ml) and dimethyl oxalate (38 mg, 0.32 mmol) was added. The mixture was heated under reflux for 24 hours. The mixture was then evaporated in vacuo. The residue was recrystallized from ethyl acetate. The product was obtained as a colorless solid.

1.5 Preparation of (4aRS,5SR,8aRS)-5-amino-1-benzylperhydroquinoxaline-2,3-dione (4aRS,5SR,8aRS)-1-Benzyl-5-(benzylamino)perhydroquinoxaline-2,3-dione (1.19 g, 3.28 mmol) was dissolved in methanol (40 ml) and $NH_4HCO_2$ (2.07 g, 32.8 mmol) was added. 120 mg of palladium-on-carbon (Merck) was furthermore added. The mixture was heated under reflux for 2 hours. The catalyst was then filtered off and the mixture was evaporated in vacuo. The residue was taken up in $CH_2Cl_2$ and the mixture was washed three times with 0.1 N NaOH. The organic phase was dried over $Na_2SO_4$ and evaporated in vacuo. A colorless solid was obtained.

1.6 Preparation of (4aRS,5SR,8aRS)-1-benzyl-5-(pyrrolidin-1-yl)perhydroquinoxaline-2,3-dione (4aRS,5SR,8aRS)-5-Amino-1-benzylperhydroquinoxaline-2,3-dione (3.06 g, 11.2 mmol) was dissolved in $CH_3CN$ (300 ml). $NaHCO_3$ (6.4 g, 76.2 mmol) and 1,4-diiodobutane (13.9 g, 44.8 mmol, 5.9 ml) were added and the mixture was heated under reflux for 18 hours. $NaHCO_3$ was separated off with a blue-band filter (Schleicher&Schuell) and the yellow solution was concentrated in vacuo. The solid was taken up in $CH_2Cl_2$ and the mixture was extracted by shaking three times with HCl (1 N). The aqueous phase was then brought to pH 8 with NaOH (2 N) and extracted by shaking three times with $CH_2Cl_2$. The organic phases were dried over $Na_2SO_4$ and evaporated in vacuo. A pale yellow solid was obtained.

1.7 Preparation of (4aRS,5SR,8aRS)-1-benzyl-5-(pyrrolidin-1-yl)perhydroquinoxaline Preparation of $Al(AlH_4)_3$:

Dried $AlCl_3$ (45 mg, 0.33 mmol) was introduced into a Schlenk flask at 0° C. under a nitrogen atmosphere and absolute THF (2.5 ml) was added. The clear, colorless solution formed was stirred at 0° C. for 5 minutes. 1.0 M $LiAlH_4$ solution (1.0 ml, 1.0 mmol) was then added dropwise. The suspension was warmed to room temperature and stirred for 20 minutes. A suspension with 1.33 mmol of $Al(AlH_4)_3$ was formed.

Reduction:

(4aRS,5SR,8aRS)-1-Benzyl-5-(pyrrolidin-1-yl)perhydroquinoxaline-2,3-dione (59 mg, 0.18 mmol) was dissolved in abs. THF (3 ml) and the solution was added to the $Al(AlH_4)_3$ suspension cooled to 0° C. The suspension was stirred at 0° C. for 45 minutes, warmed to room temperature and stirred for a further 20 minutes. Thereafter, 2 N NaOH (2 ml) was cautiously added dropwise, while cooling with ice. The suspension was extracted by shaking five times with $CH_2Cl_2$ (15 ml). The combined organic phases were dried over $Na_2SO_4$ and evaporated in vacuo. The product was obtained as a pale yellow solid.

1.8 Preparation of 1-[(4aRS,8SR,8aRS)-4-benzyl-8-(pyrrolidin-1-yl)perhydroquinoxalin-1-yl]-2-(3,4-dichlorophenyl)ethan-1-one (4aRS,5SR,8aRS)-1-Benzyl-5-(pyrrolidin-1-yl)perhydroquinoxaline (325 mg, 1.09 mmol) was dissolved in abs. $CH_2Cl_2$ (35 ml). 2-(3,4-Dichlorophenyl)acetyl chloride (291 mg, 1.3 mmol) was added dropwise and the mixture was stirred at room temperature. After 30 minutes, 2 N NaOH (35 ml) was added and the mixture was stirred vigorously for 2 hours. The aqueous phase was separated off. The organic phase was extracted by shaking three times with HCl (1 N). The aqueous phase was then brought to pH 8 with NaOH (2 N) and extracted by shaking three times with $CH_2Cl_2$. The organic phases were dried over $Na_2SO_4$ and evaporated in vacuo. A pale yellow solid was obtained.

1.9 Preparation of 2-(3,4-dichlorophenyl)-1-[(4aRS,8SR,8aRS)-8-(pyrrolidin-1-yl)-perhydroquinoxalin-1-yl]-ethan-1-one 1-[(4aRS,8SR,8aRS)-4-Benzyl-8-(pyrrolidin-1-yl)perhydroquinoxalin-1-yl]-2-(3,4-dichlorophenyl)ethan-1-one (244 mg, 0.50 mmol) was dissolved in $THF/H_2O$ (1:1, 50 ml), and conc. HCl (5 ml) and palladium-on-carbon (Pd/C) (Merck) (98.4 mg) were added. The mixture was stirred under 1 bar of $H_2$ at room temperature for 30 minutes. The catalyst was filtered off and THF was evaporated off in vacuo. The aqueous phase was brought to pH 8 with NaOH (2 N) and extracted by shaking five times with $CH_2Cl_2$. The combined organic phases were dried over $Na_2SO_4$ and evaporated. The yellowish residue was purified by column chromatography over silica gel 60 (40-63 μm, (Merck) column Ø 3 cm, $CH_2Cl_2/MeOH/NH_3$ 9:1:0.1, l=17 cm, V=10 ml) and gave a yellow resin.

Example 2

Preparation of the Diastereomer Mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one The preparation was carried out starting from (4aRS,5SR,8aRS)-5-amino-1-benzylperhydroquinoxaline-2,3-dione, which was prepared as described in Example 1.1 to 1.5.

2.1 Preparation of (4aRS,5SR,8aRS)-1-benzyl-5-(3-hydroxypyrrolidin-1-yl)perhydroquinoxaline-2,3-dione (4aRS,5SR,8aRS)-5-Amino-1-benzylperhydroquinoxaline-2,3-dione (144 mg, 0.53 mmol) was dissolved in acetonitrile (16 ml), and $NaHCO_3$ (300 mg, 3.57 mmol) and racemic 1,4-dibromobutan-2-ol (purity 85%, 1.15 g, 4.20 mmol, 0.57 ml) were added. After 24 hours, $NaHCO_3$ was separated off and the mixture was evaporated in vacuo. The solid was taken up in $CH_2Cl_2$ and the mixture was extracted by shaking three times with HCl (1 N). The aqueous phase was then brought to pH 8 with NaOH (2 N) and extracted by shaking three times with $CH_2Cl_2$. The organic phases were dried over $Na_2SO_4$ and evaporated in vacuo. The crude product was purified by flash chromatography over silica gel 60 (40-63 μm, (Merck) Ø 2 cm, acetone/MeOH/$Et_2NH$ 9.5:0.5:0.1, l=17 cm, V=5 ml). A pale yellow solid was isolated.

2.2 Preparation of (4aRS,5SR,8aRS]-1-benzyl-5-(3SR)- and (3RS)-hydroxypyrrolidin-1-yl)-perhydroquinoxaline Preparation of $Al(AlH_4)_3$:
Dried $AlCl_3$ (940 mg, 6.8 mmol) was introduced into a Schlenk flask at 0° C. under a nitrogen atmosphere and abs. THF (52 ml) was added. The clear, colorless solution formed was stirred at 0° C. for 5 minutes. 1.0 M $LiAlH_4$ solution (21 ml, 21 mmol) was then added dropwise. The suspension was warmed to room temperature and stirred for 20 minutes. A suspension with 27.8 mmol of $Al(AlH_4)_3$ was formed.
Reduction:
(4aRS,5SR,8aRS)-1-Benzyl-5-(3-hydroxypyrrolidin-1-yl)perhydroquinoxaline-2,3-dione (1.29 g, 3.8 mmol) was dissolved in abs. THF (65 ml) and the solution was added to the $Al(AlH_4)_3$ suspension cooled to 0° C. The suspension was stirred at 0° C. for 45 minutes, warmed to room temperature and stirred for a further 20 minutes. Thereafter, 2 N NaOH (13 ml) was cautiously added dropwise, while cooling with ice. The suspension was extracted by shaking five times with $CH_2Cl_2$ (50 ml). The combined organic phases were dried over $Na_2SO_4$ and evaporated in vacuo. The product was obtained as a pale yellow solid.

2.3 Preparation of 1-{(4aRS,8SR,8aSR)-4-benzyl-8-[(3SR)- and (3RS)-3-hydroxypyrrolidin-1-yl]perhydroquinoxalin-1-yl}-2-(3,4-dichlorophenyl)ethan-1-one (4aRS,5SR,8aRS)-1-Benzyl-5-((3SR)- and (3RS)-hydroxypyrrolidin-1-yl)-perhydroquinoxaline (2.6 g, 8.1 mmol) was dissolved in abs. $CH_2Cl_2$ (200 ml), 2-(3,4-dichlorophenyl)acetyl chloride (1.8 g, 8.1 mmol) was added dropwise and the mixture was stirred at room temperature. After 30 minutes, NaOH (2 N, 200 ml) was added and the reaction mixture was stirred vigorously overnight. The aqueous phase was separated off. The organic phase was extracted by shaking three times with HCl (1 N). The aqueous phase was then brought to pH 8 with NaOH (2 N) and extracted by shaking three times with $CH_2Cl_2$. The organic phases were dried over $Na_2SO_4$ and evaporated in vacuo. A pale yellow solid was isolated.

2.4 Preparation of 2-(3,4-dichlorophenyl)-1-{(4aRS,8SR,8aSR)-8-[(3SR)- and (3RS)-3-hydroxypyrrolidin-1-yl]perhydroquinoxalin-1-yl}ethan-1-one 1-{(4aRS,8SR,8aSR)-4-Benzyl-8-[(3SR)- and (3RS)-3-hydroxypyrrolidin-1-yl]perhydroquinoxalin-1-yl}-2-(3,4-dichlorophenyl)ethan-1-one (373 mg, 0.74 mmol) was dissolved in $THF/H_2O$ (1:1, 74 ml), and concentrated HCl (7.4 ml) and 158 mg of palladium-on-carbon (Merck) were added. The mixture was stirred under 1 bar of $H_2$ at room temperature for 30 minutes. The catalyst was filtered off and THF was evaporated off in vacuo. The aqueous phase was brought to pH 8 with NaOH (2 N) and extracted by shaking five times with $CH_2Cl_2$. The combined organic phases were dried over $Na_2SO_4$ and evaporated. The yellowish residue was purified by column chromatography over silica gel 60 (40-63 μm, (Merck) Ø 3 cm, $CH_2Cl_2/MeOH/NH_3$ 9:1:0.1, l=18 cm, V=10 ml) and gave a slightly yellow resin.

Example 3

Preparation of 1-[(4aRS,8SR,8aRR)-4-benzyl-8-(pyrrolidin-1-yl]perhydroquinoxalin-1-yl}-2-(3,4-dichlorophenyl)ethan-1-one The preparation was carried out starting from (4aRS,5SR,8aRS)-1-benzyl-5-(pyrrolidin-1-yl)perhydroquinoxaline-2,3-dione, which was prepared as described in Example 1.1 to 1.6.

3.1 Preparation of (4aRS,5SR,8aRS)-1-benzyl-5-(pyrrolidin-1-yl)perhydroquinoxaline Preparation of Al(AlH$_4$)$_3$:

Dried AlCl$_3$ (45 mg, 0.33 mmol) was introduced into a Schlenk flask at 0° C. under a nitrogen atmosphere and absolute THF (2.5 ml) was added. The clear, colorless solution formed was stirred at 0° C. for 5 minutes. 1.0 M LiAlH$_4$ solution (1.0 ml, 1.00 mmol) was then added dropwise. The suspension was warmed to room temperature and stirred for 20 minutes. A suspension with 1.33 mmol of Al(AlH$_4$)$_3$ was formed.

Reduction:

(4aRS,5SR,8aRS)-1-Benzyl-5-(pyrrolidin-1-yl)perhydroquinoxaline-2,3-dione (59 mg, 0.18 mmol) was dissolved in absolute THF (3 ml) and the solution was added to the Al(AlH$_4$)$_3$ suspension, cooled to 0° C. The suspension was stirred at 0° C. for 45 minutes, warmed to room temperature and stirred for a further 20 minutes. Thereafter, 2 N NaOH (2 ml) was cautiously added dropwise, while cooling with ice. The suspension was extracted by shaking five times with CH$_2$Cl$_2$ (15 ml). The combined organic phases were dried over Na$_2$SO$_4$ and evaporated in vacuo. The product was obtained as a pale yellow solid.

3.2 Preparation of 1-[(4aRS,8SR,8aRS)-4-benzyl-8-(pyrrolidin-1-yl)perhydroquinoxalin-1-yl]-2-(3,4-dichlorophenyl)ethan-1-one (4aRS,5SR,8aRS)-1-Benzyl-5-(pyrrolidin-1-yl)perhydroquinoxaline (325 mg, 1.09 mmol) was dissolved in absolute CH$_2$Cl$_2$ (35 ml). 2-(3,4-Dichlorophenyl)acetyl chloride (291 mg, 1.3 mmol) was added dropwise and the mixture was stirred at room temperature. After 30 minutes, 2 N NaOH (35 ml) was added and the mixture was stirred vigorously for 2 hours. The aqueous phase was separated off. The organic phase was extracted by shaking three times with HCl (1 N). The aqueous phase was then brought to pH 8 with NaOH (2 N) and extracted by shaking three times with CH$_2$Cl$_2$. The organic phases were dried over Na$_2$SO$_4$ and evaporated in vacuo. The product was obtained as a pale yellow solid.

Example 4

Preparation of <(3SR)- and (3RS)-1-{(4aRS,5RS,8aSR)-4-[2-(3,4-dichlorophenyl)acetyl]-perhydroquinoxalin-5-yl}pyrrolidin-3-yl>-2-(3,4-dichlorophenyl)acetate The preparation was carried out starting from (4aRS,5SR,8aRS)-1-benzyl-5-((3SR)- and (3RS)-hydroxypyrrolidin-1-yl)-perhydroquinoxaline, which was prepared as described in Example 2.1 to 2.2.

4.1 Preparation of <(3SR)- and (3RS)-1-{(4aRS,5RS,8aSR)-1-benzyl-4-[2-(3,4-dichlorophenyl)acetyl]-perhydroquinoxalin-5-yl}pyrrolidin-3-yl)-2-(3,4-dichlorophenyl)acetate (4aRS,5SR,8aRS)-1-Benzyl-5-((3SR)- and (3RS)-hydroxypyrrolidin-1-yl)-perhydroquinoxaline (0.70 g, 2.2 mmol) was dissolved in absolute CH$_2$Cl$_2$ (100 ml). 2-(3,4-Dichlorophenyl)acetyl chloride (1.1 g, 4.9 mmol) was added dropwise and the mixture was stirred at room temperature. After 4 hours, 2 N NaOH (4.5 ml) was added and the mixture was stirred vigorously overnight. The organic phase was separated off and the residue was washed twice with 2 N NaOH. The organic phase was then dried over Na$_2$SO$_4$ and evaporated in vacuo. The residue was purified twice by flash chromatography over silica gel 60 (40-63 µm, (Merck) column Ø 2 cm, EA/Et$_2$NH 10:0.1; l=15 cm, V=5 ml). A pale yellow resin was isolated.

4.2 Preparation of <(3SR)- and (3RS)-1-{(4aRS,5RS,8aSR)-4-[2-(3,4-dichlorophenyl)acetyl]-perhydroquinoxalin-5-yl}pyrrolidin-3-yl>-2-(3,4-dichlorophenyl)acetate <(3SR)- and (3RS)-1-{(4aRS,5RS,8aSR)-1-benzyl-4-[2-(3,4-dichlorophenyl)acetyl]-perhydroquinoxalin-5-yl}pyrrolidin-3-yl>-2-(3,4-dichlorophenyl)acetate (299 mg, 0.43 mmol) was dissolved in THF/H$_2$O (1:1, 59 ml), and concentrated HCl (5.9 ml) and Pd/C (81 mg) were added. The mixture was stirred under 1 bar of H$_2$ at room temperature for 35 minutes. The catalyst was filtered off and the methanol of the filtrate was evaporated off in vacuo. The aqueous phase was brought to pH 8 with NaOH (2 N) and extracted by shaking five times with CH$_2$Cl$_2$. The organic phase was dried over Na$_2$SO$_4$ and evaporated. The yellowish residue was purified by column chromatography (Ø 2 cm, CH$_2$Cl$_2$/MeOH/NH$_3$ 9.5:0.5:0.05, l=16 cm, V=5 ml). The product fractions were evaporated, the residue was taken up in CH$_2$Cl$_2$ and the solution was extracted by shaking three times with HCl (1 N). The aqueous phase was then brought to pH 8 with NaOH (2 N) and extracted by shaking three times with CH$_2$Cl$_2$. The organic phases were dried over Na$_2$SO$_4$ and evaporated in vacuo. The yellowish residue was purified by column chromatography (Ø 2 cm, CH$_2$Cl$_2$/MeOH/NH$_3$ 9:1:0.05, l=15 cm, V=5 ml) and gave a yellowish solid.

Example 5

Preparation of 1-{(4aRS,8SR,8aSR)-4-benzyl-8-[(3SR)- and (3RS)-3-hydroxypyrrolidin-1-yl]perhydroquinoxalin-1-yl}-2-(3,4-dichlorophenyl)ethan-1-one The preparation was carried out starting from (4aRS,5SR,8aRS)-1-benzyl-5-((3SR)- and (3RS)-hydroxypyrrolidin-1-yl)-perhydroquinoxaline, which was prepared as described in Example 2.1 to 2.2.

(4aRS,5SR,8aRS)-1-Benzyl-5-((3SR)- and (3RS)-hydroxypyrrolidin-1-yl)-perhydroquinoxaline (2.6 g, 8.1 mmol) was dissolved in absolute CH$_2$Cl$_2$ (200 ml), 2-(3,4-dichlorophenyl)acetyl chloride (1.8 g, 8.1 mmol) was added dropwise and the mixture was stirred at room temperature. After 30 minutes, NaOH (2 N, 200 ml) was added and the reaction mixture was stirred vigorously overnight. The aqueous phase was separated off. The organic phase was extracted by shaking three times with HCl (1 N). The aqueous phase was then brought to pH 8 with NaOH (2 N) and extracted by shaking three times with $CH_2Cl_2$. The organic phases were dried over $Na_2SO_4$ and evaporated in vacuo. A pale yellow solid was isolated.

Example 6

Preparation of 1-[(4aRS,8SR,8aRS)-4-benzoyl-8-(pyrrolidin-1-yl)-perhydroquinoxalin-1-yl]-2-(3,4-dichlorophenyl)ethan-1-one The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

Under $N_2$, 2-(3,4-dichlorophenyl)-1-[(4aRS,8SR,8aRS)-8-(pyrrolidin-1-yl)-perhydroquinoxalin-1-yl]-ethan-1-one (111 mg, 0.28 mmol) was dissolved in absolute $CH_2Cl_2$ (14 ml) and benzoyl chloride (47 mg, 0.35 mmol) was added dropwise. The mixture was stirred at room temperature overnight and then evaporated in vacuo. The residue was purified by flash chromatography (Ø 2 cm, $CH_2Cl_2$/MeOH/$NH_3$ 9.5:0.5:0.05, l=15 cm, V=5 ml) and was obtained as a yellowish resin.

Example 7

Preparation of 1-[(4aRS,8SR,8aRS)-4-acetyl-8-(pyrrolidin-1-yl)-perhydroquinoxalin-1-yl]-2-(3,4-dichlorophenyl)ethan-1-one The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

Under $N_2$, 2-(3,4-dichlorophenyl)-1-[(4aRS,8SR,8aRS)-8-(pyrrolidin-1-yl)-perhydroquinoxalin-1-yl]-ethan-1-one (113 mg, 0.29 mmol) was dissolved in absolute $CH_2Cl_2$ (14 ml) and acetyl chloride (27 mg, 0.34 mmol) was added dropwise. The mixture was stirred at room temperature overnight and then evaporated in vacuo. The residue was purified by flash chromatography (Ø 2 cm, $CH_2Cl_2$/MeOH/$NH_3$ 9.5:0.5:0.05, l=15 cm, V=5 ml). A yellowish resin was obtained.

Example 8

Preparation of 1-{(4aRS,8SR,8aRS)-1-[2-(3,4-dichlorophenyl)acetyl]-8-(pyrrolidin-1-yl)-perhydroquinoxalin-4-yl}propan-1-one The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

Under $N_2$, 2-(3,4-dichlorophenyl)-1-[(4aRS,8SR,8aRS)-8-(pyrrolidin-1-yl)-perhydroquinoxalin-1-yl]-ethan-1-one (40.7 mg, 0.10 mmol) was dissolved in absolute $CH_2Cl_2$ (5 ml) and propionyl chloride (11.4 mg, 0.12 mmol) was added dropwise. The mixture was stirred at room temperature for 2.5 hours and then evaporated in vacuo. The residue was purified by flash chromatography (Ø 2 cm, $CH_2Cl_2$/MeOH/$NH_3$ 9:1:0.1, l=16 cm, V=3 ml). A yellow resin was obtained.

Example 9

Preparation of methyl{(4aRS,8SR,8aRS)-1-[2-(3,4-dichlorophenyl)acetyl]-8-(pyrrolidin-1-yl)-perhydroquinoxalin-4-yl}carboxylate For better clarity, in this and the following compounds the numbering of the quinoxaline ring of 2-(3,4-dichlorophenyl)-1-[(4aRS,8SR,8aRS)-8-(pyrrolidin-1-yl)-perhydroquinoxalin-1-yl]-ethan-1-one is adopted.

The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

2-(3,4-Dichlorophenyl)-1-[(4aRS,8SR,8aRS)-8-(pyrrolidin-1-yl)-perhydroquinoxalin-1-yl]-ethan-1-one (100.9 mg, 0.25 mmol) was dissolved in absolute $CH_2Cl_2$ (13 ml) under a nitrogen atmosphere and methyl chloroformate (28.9 mg, 0.31 mmol) was added dropwise. The solution was stirred at room temperature for 2 hours. Thereafter, the mixture was evaporated in vacuo and the residue was purified by flash chromatography (Ø 2 cm, $CH_2Cl_2$/MeOH/$NH_3$ 9.5:0.5:0.05, l=16 cm, V=5 ml) and was obtained as a yellow resin.

Example 10

Preparation of ethyl{(4aRS,8SR,8aRS)-1-[2-(3,4-dichlorophenyl)acetyl]-8-(pyrrolidin-1-yl)-perhydroquinoxalin-4-yl}carboxylate The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

2-(3,4-Dichlorophenyl)-1-[(4aRS,8SR,8aRS)-8-(pyrrolidin-1-yl)-perhydroquinoxalin-1-yl]-ethan-1-one (104.9 mg, 0.26 mmol) was dissolved in absolute $CH_2Cl_2$ (13 ml) under $N_2$ and ethyl chloroformate (34.5 mg, 0.32 mmol) was added dropwise. The solution was stirred at room temperature overnight, and then evaporated in vacuo. The residue was purified by flash chromatography (Ø 2 cm, $CH_2Cl_2$/MeOH/$NH_3$ 9.5:0.5:0.05, l=18 cm, V=5 ml). A yellow resin was obtained.

Example 11

Preparation of 3-{(4aRS,8SR,8aRS)-1-[2-(3,4-dichlorophenyl)acetyl]-8-(pyrrolidin-1-yl)-perhydroquinoxalin-4-yl}-3-oxopropionic acid The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

Under $N_2$, 2-(3,4-dichlorophenyl)-1-[(4aRS,8SR,8aRS)-8-(pyrrolidin-1-yl)-perhydroquinoxalin-1-yl]-ethan-1-one (103 mg, 0.26 mmol) was dissolved in absolute $CH_2Cl_2$ (13 ml) and malonic acid monomethyl ester chloride (42 mg, 0.31 mmol) was added dropwise. The mixture was stirred at room temperature overnight and then evaporated in vacuo. The residue was taken up in 20 ml and 2 N NaOH (2 ml) was added. The solution was stirred at room temperature overnight. Thereafter, the mixture was evaporated in vacuo and the residue was purified by flash chromatography (Ø 2 cm, $CH_2Cl_2$/MeOH/$NH_3$ 8:2:0.1, l=15 cm, V=5 ml). The crude product was taken up in $CH_2Cl_2$ again, the mixture was filtered with a glass filter crucible G4 and Celite® (kieselguhr from CELITE Corp., Lompoc, USA) and the filtrate was evaporated in vacuo. A colorless solid was obtained.

Example 12

Preparation of 4-{(4aRS,8SR,8aRS)-1-[2-(3,4-dichlorophenyl)acetyl]-8-(pyrrolidin-1-yl)-perhydroquinoxalin-4-yl}-4-oxobutyric acid The preparation was carried out starting from 2-(3,4-dichlorophenyl)-1-[(4aRS,8SR,8aRS)-8-(pyrrolidin-1-yl)- perhydroquinoxalin-1-yl]-ethan-1-one, which was prepared as described in Example 1.1 to 1.9.

2-(3,4-Dichlorophenyl)-1-[(4aRS,8SR,8aRS)-8-(pyrrolidin-1-yl)-perhydroquinoxalin-1-yl]-ethan-1-one (108.6 mg, 0.27 mmol) was dissolved in absolute $CH_2Cl_2$ (14 ml) under $N_2$ in a 50 ml Schlenk flask. Succinic anhydride (33 mg, 0.33 mmol) and a spatula-tip of 4-(dimethylamino)pyridine (DMAP) were added to the solution. The mixture was stirred at room temperature overnight. The mixture was then evaporated almost to dryness in vacuo and the residue was purified by flash chromatography (Ø 2 cm, $CH_2Cl_2$/MeOH/$NH_3$ 8:2:0.1, l=17 cm, V=5 ml). The fractions with the product were evaporated in vacuo and the residue was taken up in $CH_2Cl_2$ again. The mixture was filtered with a glass filter crucible G4 and Celite and the filtrate was evaporated in vacuo. The yield gave a yellowish solid.

Example 13

Preparation of methyl 3-{(4aRS,8SR,8aRS)-1-[2-(3,4-dichlorophenyl)acetyl]-8-(pyrrolidin-1-yl)-perhydroquinoxalin-4-yl}-3-oxopropionate The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

Under $N_2$, 2-(3,4-dichlorophenyl)-1-[(4aRS,8SR,8aRS)-8-(pyrrolidin-1-yl)-perhydroquinoxalin-1-yl]-ethan-1-one (101 mg, 0.26 mmol) was dissolved in absolute $CH_2Cl_2$ (13 ml) and malonic acid monomethyl ester chloride (42 mg, 0.31 mmol) was added dropwise. The mixture was stirred at room temperature overnight and then evaporated in vacuo. The residue was purified by flash chromatography (Ø 2 cm, $CH_2Cl_2$/MeOH/$NH_3$ 9.5:0.5:0.05, l=15 cm, V=5 ml). A yellowish resin was obtained.

Example 14

Preparation of 1-{(4aRS,8SR,8aSR)-4-benzoyl-8-[(3SR)- and (3RS)-3-hydroxypyrrolidin-1-yl]-perhydroquinoxalin-1-yl}-2-(3,4-dichlorophenyl)ethan-1-one The preparation was carried out starting from the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one, which was prepared as described in Example 2.1 to 2.4.

Under $N_2$, the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one (120 mg, 0.29 mmol) was dissolved in absolute $CH_2Cl_2$ (18 ml) and benzoyl chloride (23 mg, 0.29 mmol) was added dropwise. The mixture was stirred at room temperature for 3 hours and then evaporated in vacuo. The residue was purified by flash chromatography (Ø 2 cm, $CH_2Cl_2$/MeOH/$NH_3$ 9:1:0.05, l=15 cm, V=5 ml). The product fractions were evaporated and the residue was taken up in $CH_2Cl_2$. The organic phase was extracted by shaking three times with HCl (1 N). The aqueous phase was brought to pH 8 with NaOH (2 N) and extracted by shaking three times with $CH_2Cl_2$. The organic phases were dried over $Na_2SO_4$ and evaporated in vacuo. The residue was purified by flash chromatography (Ø 2 cm, $CH_2Cl_2$/MeOH/$NH_3$ 9.5:0.5:0.05, l=15 cm, V=5 ml). The product fractions were evaporated. The residue was purified by preparative HPLC (MeOH/$H_2O$/$Et_2NH$ 70:30:0.1) as described in the following.

For this, a pump L-7150, autosampler L-7200, UV detector L-7400, interface D-7000 and software HSM (all from Merck Hitachi) was used. The solutions were prepared individually or a methanol/water mixture with 0.1% of diethylamine was used. The flow rate was 9.000 ml/min. A Phenomenex Gemini 5 µm C18 110A column was used. The procedure was carried out at room temperature. The injection volume was 400 µl. The detection was carried out at 225 nm. The residue was dissolved in MeOH (500 µl). 400 µl were injected (80% of the total amount of substance), and the remaining 100 µl were topped up to 500 µl with MeOH. 400 µl from this solution were injected again in a second run, so that 96% of the sample in total was purified by chromatography in two runs.

MeOH was evaporated off from the product fraction, the aqueous phase was extracted by shaking three times with $CH_2Cl_2$ and the combined organic phases were dried over $Na_2SO_4$ and evaporated. A colorless solid was isolated.

Example 15

Preparation of methyl{(4aRS,8SR,8aRS)-1-[2-(3,4-dichlorophenyl)acetyl]-8-[(3SR)- and (3RS)-3-hydroxypyrrolidin-1-yl]-perhydroquinoxalin-4-yl}carboxylate The preparation was carried out starting from the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one, which was prepared as described in Example 2.1 to 2.4.

Under $N_2$, the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one (132 mg, 0.32 mmol) was dissolved in absolute $CH_2Cl_2$ (20 ml) and methyl chloroformate (30 mg, 0.32 mmol) was added dropwise. The mixture was stirred at room temperature for 3 hours and then evaporated in vacuo. The residue was purified by flash chromatography (Ø 2 cm, $CH_2Cl_2$/MeOH/$NH_3$ 9:1:0.05, l=15 cm, V=5 ml). The product fractions were evaporated and the residue was purified by preparative HPLC (as described under Example 14 in MeOH/$H_2O$/$Et_2NH$ 70:30:0.1). MeOH was evaporated off from the product fraction in vacuo, the aqueous phase was extracted by shaking three times with $CH_2Cl_2$ and the combined organic phases were dried over $Na_2SO_4$ and evaporated. A pale yellow resin was isolated.

Example 16

Preparation of 3-{(4aRS,8SR,8aRS)-1-[2-(3,4-dichlorophenyl)acetyl]-8-[(3SR)- and (3RS)-3-hydroxypyrrolidin-1-yl]-perhydroquinoxalin-4-yl}-3-oxopropionic acid The preparation was carried out starting from the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{

(4aRS,8SR,8aSR)-8-[(3RS)-3-hydroxypyrrolidin-1-yl]perhydroquinoxalin-1-yl}ethan-1-one, which was prepared as described in Example 2.1 to 2.4.

Under $N_2$, the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one (104 mg, 0.25 mmol) was dissolved in absolute $CH_2Cl_2$ (15 ml) and malonic acid monomethyl ester chloride (34 mg, 0.25 mmol) was added dropwise. The mixture was stirred at room temperature for 3.5 hours and then evaporated in vacuo. The residue was taken up in MeOH (20 ml) and 2 N NaOH (2 ml) was added. The solution was stirred overnight and then evaporated in vacuo. The residue was purified twice by flash chromatography (1. Ø 2 cm, $CH_2Cl_2$/MeOH/$NH_3$ 8:2:0.1, l=15 cm, V=5 ml; 2. Ø 1 cm, $CH_2Cl_2$/MeOH/$NH_3$ 8:2:0.2, l=14 cm, V=3 ml). The residue was purified by preparative HPLC (as described under Example 14 in MeOH/$H_2O$/$Et_2NH$ 40:60:0.1). MeOH was evaporated off from the product fraction, the aqueous phase was extracted by shaking three times with $CH_2Cl_2$ and the combined organic phases were dried over $Na_2SO_4$ and evaporated. A colorless oil was isolated.

Example 17

Preparation of methyl 3-{(4aRS,8SR,8aRS)-1-[2-(3,4-dichlorophenyl)acetyl]-8-[(3SR)- and (3RS)-3-hydroxypyrrolidin-1-yl]-perhydroquinoxalin-4-yl}-3-oxopropionate The preparation was carried out starting from the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one, which was prepared as described in Example 2.1 to 2.4.

Under $N_2$, the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one (204 mg, 0.49 mmol) was dissolved in absolute $CH_2Cl_2$ (30 ml) and malonic acid monomethyl ester chloride (67 mg, 0.49 mmol) was added dropwise. The mixture was stirred at room temperature for 3 hours and then evaporated in vacuo. The residue was purified by flash chromatography (Ø 2 cm, $CH_2Cl_2$/MeOH/$NH_3$ 9:1:0.05, l=15 cm, V=5 ml). A yellowish resin was obtained.

Example 18

Preparation of 2-(3,4-dichlorophenyl)-1-[(4aRS,8SR,8aRS)-4-methyl-8-(pyrrolidin-1-yl)-perhydroquinoxalin-1-yl]ethan-1-one The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

Formalin (37%, 223 mg, 2.7 mmol) was dissolved in 5 ml of MeOH and NaBH$_3$CN (17.2 mg, 0.27 mmol) was added. The pH was adjusted to 5 with concentrated acetic acid. 2-(3,4-Dichlorophenyl)-1-[(4aRS,8SR,8aRS)-8-(pyrrolidin-1-yl)-perhydroquinoxalin-1-yl]-ethan-1-one (109 mg, 0.27 mmol), dissolved in MeOH (15 ml), was then added to the mixture and the mixture was stirred for 1.5 hours. After addition of saturated $Na_2CO_3$ solution (12 ml), the mixture was stirred at room temperature for 15 minutes. The precipitate formed was filtered off and MeOH was evaporated off from the filtrate under 100 mbar. The aqueous phase was extracted by shaking five times with $CH_2Cl_2$ and the combined organic phases were dried over $Na_2SO_4$ and evaporated in vacuo. The residue was purified by flash chromatography (Ø 2 cm, $CH_2Cl_2$/MeOH/$NH_3$ 9.5:0.5:0.05, l=16 cm, V=5 ml). A yellowish resin was isolated.

Example 19

Preparation of 1-[(4aRS,8SR,8aRS)-4-butyl-8-(pyrrolidin-1-yl)perhydroquinoxalin-1-yl]-2-(3,4-dichlorophenyl)-ethan-1-one The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

Butyraldehyde (93 mg, 1.3 mmol) was dissolved in 5 ml of MeOH and NaBH$_3$CN (82 mg, 1.3 mmol) was added. The pH was adjusted to 5 with concentrated acetic acid. 2-(3,4-Dichlorophenyl)-1-[(4aRS,8SR,8aRS)-8-(pyrrolidin-1-yl)-perhydroquinoxalin-1-yl]-ethan-1-one (101 mg, 0.25 mmol), dissolved in MeOH (15 ml), was then added to the mixture and the mixture was stirred at room temperature overnight. After addition of saturated $Na_2CO_3$ solution (15 ml), the mixture was stirred at room temperature for 15 minutes. The precipitate formed was filtered off. The aqueous phase of the filtrate was extracted three times with $CH_2Cl_2$ and the combined organic phases were dried over $Na_2SO_4$ and evaporated in vacuo. The residue was purified by flash chromatography (Ø 2 cm, $CH_2Cl_2$/MeOH/$NH_3$ 9.5:0.5:0.1, l=15 cm, V=5 ml). A colorless resin was isolated.

Example 20

Preparation of 2-(3,4-dichlorophenyl)-1-[(4aRS,8SR,8aRS)-4-(4-methoxybenzyl)-8-(pyrrolidin-1-yl)-perhydroquinoxalin-1-yl]ethan-1-one The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

Anisaldehyde (361 mg, 2.6 mmol) was dissolved in 5 ml of MeOH and NaBH$_3$CN (170 mg, 2.6 mmol) was added. The pH was adjusted to 5 with concentrated acetic acid. 2-(3,4-Dichlorophenyl)-1-[(4aRS,8SR,8aRS)-8-(pyrrolidin-1-yl)-perhydroquinoxalin-1-yl]-ethan-1-one (105 mg, 0.26 mmol), dissolved in MeOH (15 ml), was then added to the mixture and the mixture was stirred overnight. After addition of saturated $Na_2CO_3$ solution (15 ml), the mixture was stirred at room temperature for 15 minutes. The precipitate formed was filtered off. The aqueous phase of the filtrate was washed three times with $CH_2Cl_2$ and the combined organic phases were dried over $Na_2SO_4$ and evaporated in vacuo. The residue was purified by flash chromatography (Ø 2 cm, $CH_2Cl_2$/MeOH/$NH_3$ 9.5:0.5:0.1, l=15 cm, V=5 ml). The fractions containing the product were evaporated, the residue was taken up in $CH_2Cl_2$ and the solution was extracted by shaking three times with HCl (1 N). The aqueous phase was then brought to pH 8 with NaOH (2 N) and extracted by shaking

Example 21

Preparation of 2-(3,4-dichlorophenyl)-1-{(4aRS, 8SR,8aRS)-4-[(pyridin-2-yl)methyl]-8-(pyrrolidin-1-yl)perhydroquinoxalin-1-yl}ethan-1-one The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

Pyridine-2-carbaldehyde (268 mg, 2.5 mmol) was dissolved in MeOH (5 ml) and NaBH$_3$CN (157 mg, 2.5 mmol) was added. The pH was adjusted to 5 with concentrated acetic acid. 2-(3,4-Dichlorophenyl)-1-[(4aRS,8SR,8aRS)-8-(pyrrolidin-1-yl)-perhydroquinoxalin-1-yl]-ethan-1-one (98 mg, 0.25 mmol), dissolved in MeOH (15 ml), was then added to the mixture and the mixture was stirred at room temperature overnight. After addition of saturated Na$_2$CO$_3$ solution (15 ml), the mixture was stirred at room temperature for 15 minutes. The precipitate formed was filtered off. The aqueous phase of the filtrate was extracted five times with CH$_2$Cl$_2$ and the combined organic phases were dried over Na$_2$SO$_4$ and evaporated in vacuo. The residue was purified four times by flash chromatography (in each case Ø 2 cm, l=15 cm, V=5 ml; 1. CH$_2$Cl$_2$/MeOH/NH$_3$ 9.5:0.5:0.1, 2. CH$_2$Cl$_2$/MeOH/NH$_3$ 9.5:0.5:0.1, 3. CH$_2$Cl$_2$/MeOH/NH$_3$ 9.75:0.25:0.15, 4. CH$_2$Cl$_2$/MeOH/NH$_3$ 9.5:0.5:0.15). The crude product was then purified by preparative HPLC (as described under Example 14 in MeOH/H$_2$O/Et$_2$NH 80:20:0.1). MeOH was evaporated off from the product fraction, the aqueous phase was extracted by shaking three times with CH$_2$Cl$_2$ and the combined organic phases were dried over Na$_2$SO$_4$ and evaporated. A yellowish resin was isolated.

Example 22

Preparation of 2-(3,4-dichlorophenyl)-1-{(4aRS, 8SR,8aRS)-4-[(pyridin-3-yl)methyl]-8-(pyrrolidin-1-yl)perhydroquinoxalin-1-yl}ethan-1-one The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

2-(3,4-Dichlorophenyl)-1-[(4aRS,8SR,8aRS)-8-(pyrrolidin-1-yl)-perhydroquinoxalin-1-yl]-ethan-1-one (120 mg, 0.30 mmol) was dissolved in absolute CH$_2$Cl$_2$ (10 ml), and nicotinaldehyde (65 mg, 0.61 mmol), NaBH(OAc)$_3$ (128 mg, 0.61 mmol) and glacial acetic acid (36 mg, 0.61 mmol) were added. The mixture was stirred at room temperature. After 21 hours, the same amounts of nicotinaldehyde, NaBH(OAc)$_3$ and glacial acetic acid were again added and the mixture was stirred for 3.5 hours. The mixture was then filtered and the organic phase was extracted by shaking three times with HCl (1 N). The aqueous phase was brought to pH 8 with NaOH (2 N) and extracted by shaking three times with CH$_2$Cl$_2$. The organic phases were dried over Na$_2$SO$_4$ and evaporated in vacuo. The residue was purified by preparative HPLC (as described under Example 14 in MeOH/H$_2$O/Et$_2$NH 80:20:0.1). MeOH was evaporated off from the product fraction, the aqueous phase was extracted by shaking three times with CH$_2$Cl$_2$ and the combined organic phases were dried over Na$_2$SO$_4$ and evaporated. A yellowish resin was isolated.

Example 23

Preparation of 2-(3,4-dichlorophenyl)-1-{(4aRS, 8SR,8aRS)-4-[(1H-imidazol-5-yl)methyl]-8-(pyrrolidin-1-yl)perhydroquinoxalin-1-yl}ethan-1-one The preparation was carried out starting from 2-(3,4-dichlorophenyl)-1-[(4aRS,8SR,8aRS)-8-(pyrrolidin-1-yl)-perhydroquinoxalin-1-yl]-ethan-1-one, which was prepared as described in Example 1.1 to 1.9.

2-(3,4-Dichlorophenyl)-1-[(4aRS,8SR,8aRS)-8-(pyrrolidin-1-yl)-perhydroquinoxalin-1-yl]-ethan-1-one (134 mg, 0.34 mmol) was dissolved in absolute CH$_2$Cl$_2$ (10 ml), and 1H-imidazole-5-carbaldehyde (65 mg, 0.67 mmol), NaBH(OAc)$_3$ (143 mg, 0.67 mmol) and glacial acetic acid (41 mg, 0.67 mmol) were added. The mixture was stirred at room temperature for 2.5 hours. The mixture was then filtered and the organic phase was extracted by shaking three times with HCl (1 N). The aqueous phase was brought to pH 8 with NaOH (2 N) and extracted by shaking three times with CH$_2$Cl$_2$. The organic phases were dried over Na$_2$SO$_4$ and evaporated in vacuo. The residue was purified by preparative HPLC (as described under Example 14 in MeOH/H$_2$O/Et$_2$NH 80:20:0.1). MeOH was evaporated off from the product fraction, the aqueous phase was extracted by shaking three times with CH$_2$Cl$_2$ and the combined organic phases were dried over Na$_2$SO$_4$ and evaporated. A colorless solid was isolated.

Example 24

Preparation of 2-(3,4-dichlorophenyl)-1-{(4aRS, 8SR,8aRS)-4-methyl-8-[(3SR)- and (3RS)-3-hydroxypyrrolidin-1-yl]-perhydroquinoxalin-1-yl}ethan-1-one The preparation was carried out starting from the diastereomer mixture of 2-(3,4-dichlorophenyl)-1-{(4aRS,8SR, 8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one, which was prepared as described in Example 2.1 to 2.4.

Formalin (37%, 170 mg, 2.1 mmol) was dissolved in 5 ml of MeOH and NaBH$_3$CN (132 mg, 2.1 mmol) was added. The pH was adjusted to 5 with concentrated acetic acid. The diastereomer mixture of 2-(3,4-dichlorophenyl)-1-{(4aRS, 8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one (86 mg, 0.21 mmol), dissolved in MeOH (15 ml), was then added and the mixture was stirred for 2 hours. After addition of saturated Na$_2$CO$_3$ solution (15 ml), the mixture was stirred at room temperature for 15 minutes. The precipitate formed was filtered off. MeOH was evaporated off from the filtrate under 100 mbar. The aqueous phase was extracted by shaking five times with CH$_2$Cl$_2$ and the combined organic phases were dried over Na$_2$SO$_4$ and evaporated in vacuo. The residue was purified by flash chromatography (Ø 2 cm, CH$_2$Cl$_2$/MeOH/NH$_3$ 9:1:0.1, l=16 cm, V=5 ml). A yellowish resin was isolated.

Example 25

Preparation of 2-(3,4-dichlorophenyl)-1-{(4aRS, 8SR,8aSR)-4-[(pyridin-3-yl)methyl]-8-[(3SR)- and (3RS)-3-hydroxypyrrolidin-1-yl]perhydroquinoxalin-1-yl}ethan-1-one The preparation was carried out starting from the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one, which was prepared as described in Example 2.1 to 2.4.

A solution of the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one (103 mg, 0.25 mmol) in MeOH (15 ml) was added dropwise to a solution of nicotinaldehyde (53 mg, 0.49 mmol) and $NaBH_3CN$ (157 mg, 2.5 mmol) in MeOH (5 ml). The pH was adjusted to pH 5 with concentrated acetic acid. The mixture was stirred for 2 hours. After addition of saturated $Na_2CO_3$ solution (15 ml), the mixture was stirred at room temperature for 15 minutes. The precipitate formed was filtered off and the filtrate was evaporated in vacuo. The residue was purified by flash chromatography (Ø 2 cm, $CH_2Cl_2$/MeOH/$NH_3$ 9.5:0.5:1, l=16 cm, V=3 ml). The fractions containing the product were evaporated. The residue was purified by preparative HPLC (as described under Example 14 in MeOH/$H_2O$/$Et_2NH$ 70:30:0.1). MeOH was evaporated off from the product fraction, the aqueous phase was extracted by shaking three times with $CH_2Cl_2$ and the combined organic phases were dried over $Na_2SO_4$ and evaporated. A yellowish resin was isolated.

Example 26

Preparation of 2-(3,4-dichlorophenyl)-1-{(4aRS, 8SR,8aSR)-4-[(1H-imidazol-5-yl)methyl]-8-[(3SR)- and (3RS)-3-hydroxypyrrolidin-1-yl]perhydroquinoxalin-1-yl}ethan-1-one The preparation was carried out starting from the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one, which was prepared as described in Example 2.1 to 2.4.

1H-Imidazole-5-carbaldehyde (262 mg, 2.7 mmol) was dissolved in MeOH (5 ml) and $NaBH_3CN$ (172 mg, 2.7 mmol) was added. The pH was adjusted to 5 with concentrated acetic acid. The diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one (113 mg, 0.27 mmol), dissolved in MeOH (15 ml), was then added to the mixture and the mixture was stirred for 5 hours. After addition of saturated $Na_2CO_3$ solution (15 ml), the mixture was stirred at room temperature for 15 minutes. The precipitate formed was filtered off. The filtrate was washed three times with $CH_2Cl_2$ and the combined organic phases were dried over $Na_2SO_4$ and evaporated in vacuo. The residue was purified twice by flash chromatography (Ø 2 cm, $CH_2Cl_2$/MeOH/$NH_3$ 9:1:0.1, l=15 cm, V=5 ml). The fractions containing the product were evaporated. The residue was taken up in $CH_2Cl_2$ and the mixture was extracted by shaking three times with HCl (1 N). The aqueous phase was brought to pH 8 with NaOH (2 N) and extracted by shaking three times with $CH_2Cl_2$. The organic phases were dried over $Na_2SO_4$ and evaporated in vacuo. A yellowish resin was isolated.

Example 27

Preparation of <(3SR)- and (3RS)-1-{(4aRS,5RS, 8aSR)-1-benzyl-4-[2-(3,4-dichlorophenyl)acetyl]-perhydroquinoxalin-5-yl}pyrrolidin-3-yl>-2-(3,4-dichlorophenyl)acetate The preparation was carried out starting from (4aRS,5SR,8aRS)-1-benzyl-5-((3SR)- and (3RS)-hydroxypyrrolidin-1-yl)-perhydroquinoxaline, which was prepared as described in Example 2.1 to 2.2.

(4aRS,5SR,8aRS)-1-Benzyl-5-((3SR)- and (3RS)-hydroxypyrrolidin-1-yl)-perhydroquinoxaline (0.70 g, 2.2 mmol) was dissolved in absolute $CH_2Cl_2$ (100 ml). 2-(3,4-Dichlorophenyl)acetyl chloride (1.1 g, 4.9 mmol) was added dropwise and the mixture was stirred at room temperature. After 4 hours, 2 N NaOH (4.5 ml) was added and the mixture was stirred vigorously overnight. The organic phase was separated off and the residue was washed twice with 2 N NaOH. The organic phase was then dried over $Na_2SO_4$ and evaporated in vacuo. The residue was purified twice by flash chromatography (Ø 2 cm, EA/$Et_2NH$ 10:0.1, l=15 cm, V=5 ml). A pale yellow resin was isolated.

Example 28

Investigations on Inhibition of Pain In Vivo in the Mouse

The antinociceptive activity was investigated in the phenylquinone-induced writhing test on the mouse as described in Hendershot, L. C; Forsaith, J. J. Pharmacol. Exp. Ther. 1959, 125, 237-240.

Male NMRI mice (Charles River, Germany) weighing from 25 g to 30 g were used for this. The diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one in a concentration of 3.16 mg/kg, 10 mg/kg or 21.5 mg/kg, dissolved in PEG 200 (polyethylene glycol, Merck Schuhardt OHG) or the compound 2-(3,4-dichlorophenyl)-1-[(4aRS,8SR,8aRS)-8-pyrrolidin-1-yl)-perhydroquinoxalin-1-yl]-ethan-1-one in a concentration of 10 mg/kg, dissolved in PEG 200, was in each case administered intravenously to groups of 10 animals. After 10 minutes, 0.3 ml of a 0.02% strength aqueous solution of phenylquinone (phenyl-p-benzoquinone, Sigma, Deisenhofen) was administered intraperitoneally. The phenylquinone solution was prepared with the addition of 5% of ethanol and was kept in a water-bath at 45° C.

The number of pain-induced stretching movements, so-called writhing reactions (number n), was then counted over 10 minutes. Straightening of the body with stretching of the hind extremities is called so-called writhing reactions. If a substance has an analgesic action, the number of stretching movements decreases compared with a control group which has not received the test substance.

For this, the animals were placed individually in observation cages. The number of pain-induced stretching movements 5-20 minutes after the dose of phenylquinone was then counted for 15 minutes by means of a push-button counter. Animals which received PEG 200 vehicle solution (intravenously, i.v.) and phenylquinone (intraperitoneally, i.p.) were also run as a control.

The percentage inhibition of the writhing reactions by the diastereomer mixture of 2-(3,4-dichlorophenyl)-1-{(4aRS, 8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one or 2-(3,4-dichlorophenyl)-1-[(4aRS,8SR,8aRS)-8-(pyrrolidin-1-yl)-perhydroquinoxalin-1-yl]-ethan-1-one was calculated according to the following formula (d):

$$\text{Inhibition} = 100\% - \frac{n(\text{treated animals})}{n(\text{control})} \cdot 100\% \qquad (d)$$

It was found that at a dose of 10 mg/kg of the compound 2-(3,4-dichlorophenyl)-1-[(4aRS,8SR,8aRS)-8-(pyrrolidin-1-yl)-perhydroquinoxalin-1-yl]-ethan-1-one, an inhibition of about 9% were achieved. No noticeable side effects were found.

It was furthermore found that the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one inhibited 5% of the writhing movements at a concentration of 3.16 mg/kg, 40% at a concentration of 10 mg/kg and 97% at a concentration of 21.5 mg/kg.

An analgesic action of the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one and of the compound 2-(3,4-dichlorophenyl)-1-[(4aRS, 8SR,8aRS)-8-(pyrrolidin-1-yl)-perhydroquinoxalin-1-yl]-ethan-1-one was thus found.

Example 29

Investigations on Inhibition of Pain in the Visceral Inflammation Pain Model

In this animal study, a non-neurogenic colitis (inflammation) induced by mustard oil was caused in the mouse. Various test groups within the experiments give a breakdown of the peripheral and centrally mediated analgesia of the compound investigated, 2-(3,4-dichlorophenyl)-1-[(4aRS,8SR,8aRS)-8-(pyrrolidin-1-yl)-perhydroquinoxalin-1-yl]-ethan-1-one and of the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one. Unless stated otherwise, the studies were conducted as described in Christoph, T.; Kögel, B.; Schiene, K.; Meen, M.; De Vry, J.; Friedrichs, E. Eur. J. Pharmacol. 2005, 507, 87-98.

By the behavior of the animals two to twelve minutes after rectal administration of mustard oil, the visceral spontaneous pain was recorded quantitatively here in the form of a pain score, for example by the hopping, twitching or vocalization. After 20 to 40 minutes, the abdominal wall of the animals was stimulated mechanically. Centrally mediated allodynia and hyperalgesia were ascertained by von Frey filaments (1 Nm and 16 Nm respectively).

The size of the study groups was n=7 mice. Polyethylene glycol, PEG200 (Merck Schuhardt OHG), was administered rectally to a control group of animals, and in a second group colitis was induced by rectally administered mustard oil. Mustard oil (rectally) and the diastereomer mixture of 2-(3, 4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one or 2-(3,4-dichlorophenyl)-1-[(4aRS,8SR,8aRS)-8-(pyrrolidin-1-yl)-perhydroquinoxalin-1-yl]-ethan-1-one, dissolved in PEG 200, was administered intravenously to further groups. One study group received the compound 2-(3, 4-dichlorophenyl)-1-[(4aRS,8SR,8aRS)-8-(pyrrolidin-1-yl)-perhydroquinoxalin-1-yl]-ethan-1-one here administered in a concentration of 21.5 mg/kg. Further study groups received the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one administered in concentrations of 1.0 mg/kg, 3.16 mg/kg and 10 mg/kg. 10 ml/kg were employed as the administration volume.

A reduced action in the group which received mustard oil and the diastereomer mixture or 2-(3,4-dichlorophenyl)-1-[(4aRS,8SR,8aRS)-8-(pyrrolidin-1-yl)-perhydroquinoxalin-1-yl]-ethan-1-one is an indication of an analgesic action of the compound.

The Study Procedure in Detail:

Male NMRI mice (Charles River, Germany) with a body weight of from 20 g to 35 g were acclimatized on a grating in Plexiglas cages (base area 14.5×14.5 cm, height 10 cm) for about 30 minutes.

The behavior of the mice towards ten mechanical stimulations by means of von Frey filaments (Grünenthal GmbH) with a force of 1 mN, 4 mN, 8 mN, 16 mN and 32 mN on the abdominal wall was recorded as the pre-value. The behavior was analyzed either via the sum of the number of nocifensive reactions or via the quality of these nocifensive reactions and the weighting thereof by multiplication of the number of reactions by the associated factor and then obtaining the sum. The factors in this context were the following: Factor 1: slight raising of the abdomen, licking at the stimulus site, moving away; Factor 2: stretching away of the hind paws, slight hopping away, twitching of the hind paws, jerky, marked licking of the stimulus site; Factor 3: jumping away, vocalization.

The diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one, the compound 2-(3,4-dichlorophenyl)-1-[(4aRS,8SR,8aRS)-8-(pyrrolidin-1-yl)-perhydroquinoxalin-1-yl]-ethan-1-one or 10 ml/kg of solvent, PEG 200, was then administered intravenously to the study groups.

After 5 minutes, a rectal dose of 50 µl of a 3.5% strength solution of mustard oil in PEG200 was administered.

A control group of animals received a rectal administration of 50 µl of PEG200.

2 to 12 minutes after the dose of mustard oil, the animals showed a spontaneous visceral pain behavior, which was observed. The number of reactions was multiplied by the associated factor—Factor 1: slight raising of the abdomen, licking at the stimulus site, moving away; Factor 2: stretching away of the hind paws, slight hopping away, twitching of the hind paws, jerky, marked licking of the stimulus site; Factor 3: jumping away—and the sum was then obtained, which represents the spontaneous visceral pain score.

20 to 40 minutes after the dose of mustard oil, the behavior of the animals to ten mechanical stimulations by means of von Frey filaments with 1 mN, 4 mN, 8 mN, 16 mN and 32 mN on the abdominal wall was observed again and quantified as described above.

The mechanical allodynia transmitted was determined here from the sum of the reactions to the stimulation with the von Frey filament of strength 1 mN. The mechanical hyperalgesia transmitted was determined from the sum of the weighted reactions to the stimulation with the von Frey filament of strength 16 mN.

The action of the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one and the compound 2-(3,4-dichlorophenyl)-1-[(4aRS,8SR,8aRS)-8-(pyrrolidin-1-yl)-perhydroquinoxalin-1-yl]-ethan-1-one was described in comparison with the control group by 1. inhibition of the spontaneous visceral pain behavior, 2. inhibition of the mechanical allodynia transmitted and 3. inhibition of the mechanical hyperalgesia transmitted. Statistical evaluations were performed with the program SYSTAT, version 11 for Windows.

It was found that the compound 2-(3,4-dichlorophenyl)-1-[(4aRS,8SR,8aRS)-8-(pyrrolidin-1-yl)-perhydroquinoxalin-1-yl]-ethan-1-one showed a very good action in the spontaneous pain study. The pain score corresponded to that of the control group. This indicates a good peripheral pain inhibition.

In the models of the centrally mediated types of pain, allodynia and hyperalgesia, no action of the compound 2-(3,4-dichlorophenyl)-1-[(4aRS,8SR,8aRS)-8-(pyrrolidin-1-yl)-perhydroquinoxalin-1-yl]-ethan-1-one was found.

It was furthermore found that the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one showed an analgesic effect in the spontaneous pain study with the forms of administration with increasing dose. At 10 mg/kg, absence of pain was nearly achieved.

In the models of the centrally mediated types of pain, no significant reduction in the pain was to be found.

This shows that the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one and the compound 2-(3,4-dichlorophenyl)-1-[(4aRS,8SR,8aRS)-8-(pyrrolidin-1-yl)-perhydroquinoxalin-1-yl]-ethan-1-one have a good peripheral analgesic action.

Example 30

Determination of the κ Receptor Affinity

The affinity for receptors can be determined in vitro by receptor binding studies. Membrane preparations, a radioactively labeled radioligand which has a high affinity and selectivity for the receptor and the test substance of which the affinity is to be determined are employed here.

Incubation of the receptor preparation with a ligand L leads to an equilibrium between unoccupied receptor R and free ligand L on the one hand and the receptor-ligand complex RL on the other hand.

From this, the dissociation constant $K_d$ is obtained according to the following equation (a):

$$K_d = \frac{k_2}{k_1} = \frac{[R] \cdot [L]}{[RL]} \qquad (a)$$

To determine the affinity of a test substance, competition experiments were carried out. In this context, the radioligand and the test substance to be investigated were added to the receptor material. The two ligands now entered into competition with one another for the binding sites on the receptor. After equilibrium was established, the non-bound radioligand was separated off and the radioactivity of the receptor-ligand complex was measured. Conclusions regarding the ratio of bound radioligand to bound test substance can be drawn from this, and a conclusion regarding the affinity of the test substance for the receptor can therefore be drawn. The radioactivity was measured indirectly with a scintillation counter with the aid of a scintillation cocktail which emits photons through the tritium-labeled ligand.

The measurement was performed at a constant receptor and radioligand concentration, and the concentration of test substance to be determined was varied. In addition, the values for the non-specific and the maximum binding were determined. The non-specific binding of the radioligand was determined by incubation of the receptor preparation with radioligand and a large excess of a selective ligand which is not radioactively labeled, as a result of which the specific binding sites of the receptor were satisfied with non-labeled ligand. The radioactivity measured then resulted from non-specific binding of the radioligand to the membrane, filter etc. The maximum binding was determined by incubating the receptor material with the radioligand without test substances. The percentage residual binding of the radioligand can be calculated according to equation (b):

$$\% \text{ Residual binding} = \frac{[\text{binding measured}] - [\text{non-specific binding}]}{[\text{maximum binding}] - [\text{non-specific binding}]} \cdot 100\% \qquad (b)$$

If the residual binding is plotted on a graph against the logarithm to the base ten of the substance concentration, a sigmoid curve is obtained. That concentration of test substance at which the binding of the radioligand to the receptor was reduced by 50% was determined from this. This is called the $IC_{50}$ value.

From the $IC_{50}$ value determined, with the known dissociation constant $K_d$ of the radioligand the equilibrium constant $K_i$ can be calculated according to the following Cheng and Prusoff equation (c) (Cheng, Y. C; Prusoff, W. H. Biochem. Pharmacol. 1973, 22, 3099-3108):

$$K_i = \frac{IC_{50}}{1 + \frac{[L]}{K_d}} \quad (c)$$

where $K_i$ inhibition constant of the test substance $IC_{50}$ test substance concentration at which 50% of the radioligand is displaced

[L] concentration of the radioligand $K_d$ dissociation constant of the radioligand The $K_i$ value was determined by the method according to Hunter et al., Br. J. Pharmacol. 1990, 1001. 183-189 and Smith et al., J. Neuoch. 1989, 53, 27-36, wherein a preparation from the whole guinea pig brain was used and [$^3$H]-U-69,593 (Amersham) was used as the radioligand.

The $K_i$ values were calculated from $IC_{50}$ values which were determined from competition curves with six different concentrations. In the case of compounds with a high affinity, the $K_i$ values were determined two or three times and mean values and the standard deviation (SEM, standard error of the mean) were calculated.

Test Solutions

The compound 2-(3,4-dichlorophenyl)-1-[(4aRS,8SR,8aRS)-8-(pyrrolidin-1-yl)-perhydroquinoxalin-1-yl]-ethan-1-one and the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one were in each case dissolved in dimethylsulfoxide (DMSO) without the addition of water, to give a 10 mM solution. This stock solution was then frozen at −80° C. The sample was thawed as required, and diluted with incubation buffer to the required concentration.

General Procedure

A screening was first performed with six different concentrations (concentration $c=10^{-5}$ mol/l, $10^{-6}$ mol/l. $10^{-7}$ mol/l, $10^{-8}$ mol/l, $10^{-9}$ mol/l, $10^{-10}$ mol/l). The solutions were in each case measured twice. The test runs were then carried out likewise in six different concentrations. These were chosen such that the estimated $IC_{50}$ value was in the middle region of the concentration span.

The displacement experiments were evaluated via non-linear regression with GraphPad Prism 3.0 (GraphPad software). The $IC_{50}$ values obtained were converted into $K_i$ values by the Cheng and Prusoff equation (Cheng, Y. C; Prusoff, W. H. Biochem. Pharmacol. 1973, 22, 3099-3108).

The test runs were performed three times and the mean with the standard deviation of the mean (SEM, "standard error of the mean") was obtained from the triplicate values. The particular values of the equilibrium dissociation constants of the radioligands were obtained from the literature.

Standardization of the Assays

To standardize the measurement method, the receptor preparations were diluted into various concentrations with the particular buffer and both the non-specific and the total binding were measured. The dilutions of the receptor preparations were then chosen such that the non-specific binding was about 10% of the total binding (approx. 30 of 300 cpm). By this means, a minimum concentration of desired receptor in the protein suspension was ensured. The determination of the protein concentration according to Bradford (approx. 1.5 mg/ml to 4.0 mg/ml) then followed.

Preparation of the κ Receptor Preparation

All the solutions prepared were cooled on ice. Approx. 5-6 times the amount of sucrose solution (0.32 M) was added to five guinea pig brains and the mixture was homogenized (approx. 800 to 1,000 revolutions/minute) in a Potter (Elvehjem-Potter, Braun), while cooling with ice. The homogenate was introduced into centrifuge vessels (40 ml) and centrifuged (2,900 revolutions/minute, 4° C., 10 min) in a high capacity refrigerated centrifuge (Sorvall RC-5, Thermo Fisher Scientific). The supernatant was introduced into ultracentrifuge vessels (40 ml) and centrifuged again (23,500 g, 4° C., 20 min, Sorvall RC-5, Thermo Fisher Scientific).

The supernatant of the ultracentrifugation was discarded and the pellet with a little ice-cold TRIS buffer (50 mM, pH 8.0, 1.66 g Tris-base, 5.72 g Tris-HCl, to 1 l with water). The pellet was resuspended by vigorous shaking (vortexer) and the suspension was incubated at room temperature (22° C.) for 30 minutes with continuous shaking. The suspension was then centrifuged again (23,500 g, 4° C., 20 min). The supernatant was discarded and the pellet was taken up in a little cold TRIS buffer. After homogenization in the Potter, the non-specific and the total binding were determined. The protein suspension was then diluted with TRIS buffer, so that the non-specific binding was about 10% of the total binding, and a protein determination according to Bradford was carried out (protein standard: bovine serum albumin, Sigma-Aldrich). The protein content of the preparation was as a rule approx. 1.5 mg/ml. The homogenate was transferred into 2 ml Eppendorf vessels and frozen at −81° C.

Determination of the Affinity for the κ Receptor

Starting from the 10 mM stock solution of the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one and of the compound 2-(3,4-dichlorophenyl)-1-[(4aRS,8SR,8aRS)-8-(pyrrolidin-1-yl)-perhydroquinoxalin-1-yl]-ethan-1-one, solutions of the diastereomer mixture and of the compound 2-(3,4-dichlorophenyl)-1-[(4aRS,8SR,8aRS)-8-(pyrrolidin-1-yl)-perhydroquinoxalin-1-yl]-ethan-1-one in various concentrations were prepared by dilution with buffer. [$^3$H]-U69.593 (Amersham) in TRIS buffer (50 mM, pH 7.4) was used as the radioligand. Before carrying out the binding studies, the filter mats (Filtermat A, Perkin-Elmer) were laid in polyethylenimine solution (0.2%) for 2.5 hours in order to reduce the non-specific binding. The total binding and the non-specific binding were also determined in each test run. For determination of the non-specific binding, the assay was carried out in the presence of a large excess of non-labeled U69.593 (10 μM). For measurement of the total binding, the assay was carried out without the test substance and the missing volume was replaced by buffer. In a total volume of 200 μl, 50 μl of TRIS-MgCl$_2$ buffer, 50 μl of test substance solution, 50 μl of radioligand solution (4 nM; corresponds to 1 nM in the assay) and finally 50 μl of protein solution (approx. 1.5 mg/ml) were pipetted into a well of a microtiter plate (standard 96-well multititer plats, Diagonal). After all the wells were filled, the plate was closed with a cover and shaken with a shaker (own construction) at 37° C. and approx. 500 revolutions/minute for 2.5 hours. After the incubation, the cover was removed and the plate was sucked off through a filter mat with the aid of the Unifilter 96 Harvester cell collector (Perkin-Elmer). The wells were washed with water five times under reduced pressure. After the washing, the filter mat was first predried in the opened Unifilter 96 Harvester cell collector under reduced pressure and then dried completely in a preheated drying cabinet at 95° C. for 5 minutes. Meltilex melt-on scintillator (Meltilex A, Perkin-Elmer) was then laid on the filter mat and the filter mat was heated in the drying cabinet at 95° C. for approx. 2-3 minutes, until the melt-on scintillator had penetrated the mat completely. At room temperature, the scintillator solidified again completely within 1 minute, so that the filter mat could be measured in the scintillation counter (Microbeta TRILUX, Perkin-Elmer) ([$^3$H] measurement protocol; 5 minutes measuring time per well). The $K_d$ value of the radioligand [$^3$H]-U69.593 ($K_d$=0.67 nM) was obtained from the literature.

It was found that the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one and the compound 2-(3,4-dichlorophenyl)-1-[(4aRS,8SR,8aRS)-8-(pyrrolidin-1-yl)-perhydroquinoxalin-1-yl]-ethan-1-one in each case had a high affinity for the κ receptor of 8.7±1.1 nM and 2.1±0.4 nm.

Example 31

Determination of the κ Receptor Affinity

The determination of the κ receptor affinity for the compounds listed in Tables 1 and 2 was carried out using these compounds as described under Example 30. The values for the affinity of the compounds for the κ receptor shown in the following Tables 1 and 2 were obtained.

TABLE 1

| Compound | κ: $K_i$ ± SEM/nM |
|---|---|
| 1-[(4aRS,8SR,8aRS)-4-Benzoyl-8-(pyrrolidin-1-yl)-perhydroquinoxalin-1-yl]-2-(3,4-dichlorophenyl)ethan-1-one | 15 ± 3.4 |
| 1-[(4aRS,8SR,8aRS)-4-Acetyl-8-(pyrrolidin-1-yl)-perhydroquinoxalin-1-yl]-2-(3,4-dichlorophenyl)ethan-1-one | 24 ± 2.8 |
| 1-{(4aRS,8SR,8aRS)-1-[2-(3,4-dichlorophenyl)acetyl]-8-(pyrrolidin-1-yl)-perhydroquinoxalin-4-yl}propan-1-one | 26 ± 1.3 |
| Methyl {(4aRS,8SR,8aRS)-1-[2-(3,4-dichlorophenyl)acetyl]-8-(pyrrolidin-1-yl)-perhydroquinoxalin-4-yl}carboxylate | 9.7 ± 1.8 |
| Ethyl {(4aRS,8SR,8aRS)-1-[2-(3,4-dichlorophenyl)acetyl]-8-(pyrrolidin-1-yl)-perhydroquinoxalin-4-yl}carboxylate | 15 ± 3.0 |
| 3-{(4aRS,8SR,8aRS)-1-[2-(3,4-Dichlorophenyl)acetyl]-8-(pyrrolidin-1-yl)-perhydroquinoxalin-4-yl}-3-oxopropionic acid | 169 ± 63 |
| 4-{(4aRS,8SR,8aRS)-1-[2-(3,4-Dichlorophenyl)acetyl]-8-(pyrrolidin-1-yl)perhydroquinoxalin-4-yl}-4-oxobutyric acid | 136 ± 31 |
| Methyl 3-{(4aRS,8SR,8aRS)-1-[2-(3,4-dichlorophenyl)acetyl]-8-(pyrrolidin-1-yl)-perhydroquinoxalin-4-yl}-3-oxopropionate | 11 ± 5.6 |
| 1-{(4aRS,8SR,8aRS)-4-Benzoyl-8-[(3SR)- and (3RS)-3-hydroxypyrrolidin-1-yl]perhydroquinoxalin-1-yl}-2-(3,4-dichlorophenyl)ethan-1-one | 22 ± 5.6 |
| Methyl {(4aRS,8SR,8aRS)-1-[2-(3,4-dichlorophenyl)acetyl]-8-[(3SR)- and (3RS)-3-hydroxypyrrolidin-1-yl]-perhydroquinoxalin-4-yl}carboxylate | 11 ± 2.8 |
| 3-{(4aRS,8SR,8aRS)-1-[2-(3,4-Dichlorophenyl)acetyl]-8-[(3SR)- and (3RS)-3-hydroxypyrrolidin-1-yl]-perhydroquinoxalin-4-yl}-3-oxopropionic acid | 482 ± 113 |
| Methyl 3-{(4aRS,8SR,8aRS)-1-[2-(3,4-dichlorophenyl)acetyl]-8-[(3SR)- and (3RS)-3-hydroxypyrrolidin-1-yl]-perhydroquinoxalin-4-yl}-3-oxopropionate | 18 ± 2.2 |

TABLE 2

| Compound | κ: $K_i$ ± SEM/nM |
|---|---|
| 2-(3,4-Dichlorophenyl)-1-[(4aRS,8SR,8aRS)-4-methyl-8-(pyrrolidin-1-yl)-perhydroquinoxalin-1-yl]ethan-1-one | 2.7 ± 0.6 |
| 1-[(4aRS,8SR,8aRS)-4-Butyl-8-(pyrrolidin-1-yl)-perhydroquinoxalin-1-yl]-2-(3,4-dichlorophenyl)-ethan-1-one | 3.1 ± 1.8 |
| 1-[(4aRS,8SR,8aRS)-4-Benzyl-8-(pyrrolidin-1-yl)perhydroquinoxalin-1-yl]-2-(3,4-dichlorophenyl)ethan-1-one | 9.4 ± 1.6 |
| 2-(3,4-Dichlorophenyl)-1-[(4aRS,8SR,8aRS)-4-(4-methoxybenzyl)-8-(pyrrolidin-1-yl)-perhydroquinoxalin-1-yl]ethan-1-one | 6.8 ± 2.0 |
| 2-(3,4-Dichlorophenyl)-1-{(4aRS,8SR,8aRS)-4-[(pyridin-2-yl)methyl]-8-(pyrrolidin-1-yl)perhydroquinoxalin-1-yl]ethan-1-one | 4.2 ± 2.6 |
| 2-(3,4-Dichlorophenyl)-1-{(4aRS,8SR,8aRS)-4-[(pyridin-3-yl)methyl]-8-(pyrrolidin-1-yl)perhydroquinoxalin-1-yl}ethan-1-one | 0.13 ± 0.02 |
| 2-(3,4-Dichlorophenyl)-1-{(4aRS,8SR,8aRS)-4-[(1H-imidazol-5-yl)methyl]-8-(pyrrolidin-1-yl)perhydroquinoxalin-1-yl}ethan-1-one | 4.3 ± 2.0 |
| 2-(3,4-Dichlorophenyl)-1-{(4aRS,8SR,8aRS)-4-methyl-8-[(3SR)- and 3RS)-3-hydroxypyrrolidin-1-yl]-perhydroquinoxalin-1-yl}ethan-1-one | 5.4 ± 0.8 |
| 1-{(4aRS,8SR,8aRS)-4-Benzyl-8-[(3SR)- and (3RS)-3-hydroxypyrrolidin-1-yl]perhydroquinoxalin-1-yl}-2-(3, 4-dichlorophenyl)ethan-1-one | 6.6 ± 1.4 |
| 2-(3,4-Dichlorophenyl)-1-{(4aRS,8SR,8aRS)-4-[(pyridin-3-yl)methyl]-8-[(3SR)- and (3RS)-3-hydroxypyrrolidin-1-yl]perhydroquinoxalin-1-yl}ethan-1-one | 3.8 ± 0.7 |

It was found that the compounds in each case had a high affinity for the κ receptor.

Example 32

Determination of the Selectivity of Binding to the κ Receptor

The determination of the receptor affinity in the context of the selectivity investigations was carried out in human receptor material. In this, [$^3$H]-CI-977 (TRK945, Amersham, specific activity approx. 48 Ci/mmol) was used as the radioligand for the κ receptor and [$^3$H]-naloxone (N-allyl-2,3) (NET719, NEN, specific activity approx. 60 Ci/mmol) for the μ receptor.

General Procedure (Binding of Human κ and μ Opiate Receptor Membranes)

In deviation from the test procedure described under Example 30 for κ opiate receptor binding to guinea pig brain homogenates, for determination of the binding to human κ and μ opiate receptor membranes in each case a receptor screening was performed with five different concentrations (concentration $c=10^{-5}, 10^{-6}, 10^{-7}, 10^{-8}, 10^{-9}$ mol/l in each case as duplicate values) in 2 studies independent of each other.

The evaluation and determination of the particular $IC_{50}$ values were likewise performed by means of non-linear regression calculation by the software XLfit version 4 embedded in the evaluation software ActivityBase version 5.3.4.26. $K_i$ values were calculated from the particular $IC_{50}$ values with the Cheng-Prussof equation mentioned under Example 30. For the receptor membrane preparations used, the particular values of the dissociation constants for calculation of the $K_i$ values by the Cheng-Prussof equation were determined beforehand by ligand receptor saturation experiments under the same receptor binding conditions.

Determination of the Affinity for the κ Receptor

The receptor membranes of the human κ opioid receptor from HEK-293 cells (PerkinElmer Life Sciences (order no. 6110558 #370-960-A) were thawed in warm (approx. 37° C.) water shortly (2 minutes) before use, diluted with assay buffer (50 mmol/l of TRIS-HCl, pH 7.4) supplemented with 0.02% of bovine serum albumin (Serva) in the ratio of 1:34 and homogenized in a Potter. Assay buffer (50 mmol/l of TRIS-HCl pH 7.4) was added to wheat germ agglutinin SPA ("scintillation proximity assay") beads (Amersham (order no. RPNQ0001)) (70 ml/500 mg of beads) and the beads were suspended on a magnetic stirrer for 1 hour. In each case 5 μl of the solution of the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one or of the compound 2-(3,4-dichlorophenyl)-1-[(4aRS,8SR,8aRS)-8-(pyrrolidin-1-yl)-perhydroquinoxalin-1-yl]-ethan-1-one, each of which was present dissolved in a 50 times higher concentration (in 25% strength aqueous dimethylsulfoxide (DMSO)) than the particular test concentration in the reaction mixture, 20 μl of the radioligand [³H]-CI-977 (TRK945, Amersham, specific activity approx. 48 Ci/mmol) (12.5 nmol/l of assay buffer) and 225 μl of a preincubated mixture of 88 μl of the diluted receptor membrane and 137 μl of bead suspension were now pipetted into the wells of a luminescence plate (SPA plates, Costar). For determination of the non-specific binding, instead of the solution of the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one or of the compound 2-(3,4-dichlorophenyl)-1-[(4aRS,8SR,8aSR) 8-(pyrrolidin-1-yl)-perhydroquinoxalin-1-yl]-ethan-1-one and the mixtures for determination of the non-specific binding and of the maximum binding thus contained a 0.5% strength DMSO solvent content in the final mixture. The mixtures were mixed thoroughly with a minishaker and incubated at room temperature for 90 minutes. The samples were then centrifuged at $500^{-1}$ (60 g) for 20 minutes (Omnifuge 2.0 RS, Heraeus) and the radioactivity bound to the SPA beads was measured with a scintillation counter (1450 Microbeta Trilux, Wallac/PerkinElmer Life Sciences).

It was found that the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one and the compound 2-(3,4-dichlorophenyl)-1-[(4aRS,8SR,8aRS)-8-(pyrrolidin-1-yl)-perhydroquinoxalin-1-yl]-ethan-1-one in each case had a high affinity for the κ receptor of 19 nM and 28 nM.

Determination of the Affinity for the μ Receptor

Receptor membranes of the human μ opioid receptor from CHO-K1 cells (RBHOMM) (PerkinElmer Life Sciences) were thawed in warm (37° C.) water shortly (2 minutes) before use, diluted with assay buffer (50 mmol/l of Tris-HCl, pH 7.4) supplemented with 0.06% of bovine serum albumin (Serva) and homogenized in a Potter. Assay buffer (50 mmol/l of Tris-HCl pH 7.4) was added to wheat germ agglutinin SPA ("scintillation proximity assay") beads (Amersham (order no. RPNQ0001)) (100 ml/500 mg of beads) and the beads were suspended on a magnetic stirrer for 1 hour. In each case 5 μl of the solution of the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one or of the compound 2-(3,4-dichlorophenyl)-1-[(4aRS,8SR,8aRS)-8-(pyrrolidin-1-yl)-perhydroquinoxalin-1-yl]-ethan-1-one, each of which was present dissolved in a 50 times higher concentration (in 25% strength aqueous dimethylsulfoxide (DMSO)) than the particular test concentration in the reaction mixture, 25 μl of the radioligand [³H]-naloxone (N-allyl-2,3) (NET719, NEN, specific activity approx. 60 Ci/mmol) (10 nmol/l of assay buffer) and 220 μl of a preincubated mixture of 20 μl of receptor membrane and 200 μl of bead suspension were now pipetted into the wells of a luminescence plate (SPA plates, Costar). For determination of the non-specific binding, instead of the solution of the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one or of the compound 2-(3,4-dichlorophenyl)-1-[(4aRS,8SR,8aRS)-8-(pyrrolidin-1-yl)-perhydroquinoxalin-1-yl]-ethan-1-one, 5 μl of naloxone HCl (500 μmol/l of aqueous 25% strength DMSO solution), and for determination of the total binding 5 μl of an aqueous 25% DMSO solution were added. All the reaction mixtures with various concentrations of the diastereomer mixture or of the compound 2-(3,4-dichlorophenyl)-1-[(4aRS,8SR,8aRS)-8-(pyrrolidin-1-yl)-perhydroquinoxalin-1-yl]-ethan-1-one and the mixtures for determination of the non-specific binding and of the maximum binding thus contained a 0.5% strength DMSO solvent content in the final mixture. The mixtures were mixed thoroughly with a minishaker and incubated at room temperature for 90 minutes. The samples were then centrifuged at $500^{-1}$ (60 g) for 20 minutes (Omnifuge 2.0 RS, Heraeus) and the radioactivity bound to the SPA beads was measured with a scintillation counter (1450 Microbeta Trilux, Wallac/PerkinElmer Life Sciences).

It was found that the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3- hydroxypyrrolidin-1-yl]perhydroquinoxalin-1-yl}ethan-1-one and the compound 2-(3,4-dichlorophenyl)-1-[(4aRS,8SR,8aRS)-8-(pyrrolidin-1-yl)-perhydroquinoxalin-1-yl]-ethan-1-one in each case had an affinity for the µ receptor of 4,900 nM and 2,800 nM.

By comparison, the selectivity of the binding affinity for the κ receptor compared with the µ receptor is thus 258:1 for the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one and 99:1 for the compound 2-(3,4-dichlorophenyl)-1-[(4aRS,8SR,8aRS)-8-(pyrrolidin-1-yl)-perhydroquinoxalin-1-yl]-ethan-1-one. This shows that the diastereomer mixture of 2-(3,4-dichlorophenyl)-1-{(4aRS,8SR,8aSR)-8-[(3SR)-3-hydroxypyrrolidin-1-yl]perhydroquinoxalin-1-yl}ethan-1-one and 2-(3,4-dichlorophenyl)-1-{(4aRS,8SR,8aSR)-8-[(3RS)-3-hydroxypyrrolidin-1-yl]perhydroquinoxalin-1-yl}ethan-1-one and the compound 2-(3,4-dichlorophenyl)-1-[(4aRS,8SR,8aRS)-8-(pyrrolidin-1-yl)-perhydroquinoxalin-1-yl]-ethan-1-one are distinguished by a selectivity of binding to the κ receptor compared with binding to the µ receptor.

Example 33

Determination of the Selectivity of Binding to the κ Receptor

The determination of the selectivity of binding to the κ receptor for the compounds listed in Tables 3 and 4 was carried out using these compounds as described under Example 32. The values for the selectivity of binding of the compounds to the κ receptor compared with binding to the µ receptor shown in the following Tables 3 and 4 were obtained.

TABLE 3

| Compound | Selectivity κ/µ |
| --- | --- |
| 1-[(4aRS,8SR,8aRS)-4-Benzoyl-8-(pyrrolidin-1-yl)-perhydroquinoxalin-1-yl]-2-(3,4-dichlorophenyl)ethan-1-one | 14:1 |
| 1-[(4aRS,8SR,8aRS)-4-Acetyl-8-(pyrrolidin-1-yl)-perhydroquinoxalin-1-yl]-2-(3,4-dichlorophenyl)ethan-1-one | 14:1 |
| 1-{(4aRS,8SR,8aRS)-1-[2-(3,4-dichlorophenyl) acetyl]-8-(pyrrolidin-1-yl)-perhydroquinoxalin-4-yl}propan-1-one | 8:1 |
| Methyl {(4aRS,8SR,8aRS)-1-[2-(3,4-dichlorophenyl)acetyl]-8-(pyrrolidin-1-yl)-perhydroquinoxalin-4-yl}-carboxylate | 15:1 |
| Ethyl {(4aRS,8SR,8aRS)-1-[2-(3,4-dichlorophenyl)acetyl]-8-(pyrrolidin-1-yl)-perhydroquinoxalin-4-yl}carboxylate | 10:1 |
| Methyl 3-{(4aRS,8SR,8aRS)-1-[2-(3,4-dichlorophenyl)acetyl]-8-(pyrrolidin-1-yl)-perhydroquinoxalin-4-yl}-3-oxopropionate | 22:1 |
| 1-{(4aRS,8SR,8aRS)-4-Benzoyl-8-[(3SR)- and (3RS)-3-hydroxypyrrolidin-1-yl]-perhydroquinoxalin-1-yl}-2-(3,4-dichlorophenyl)ethan-1-one | 21:1 |
| Methyl {(4aRS,8SR,8aRS)-1-[2-(3,4-dichlorophenyl)acetyl]-8-[(3SR)- and (3RS)-3-hydroxypyrrolidin-1-yl]-perhydroquinoxalin-4-yl}carboxylate | 43:1 |
| Methyl 3-{(4aRS,8SR,8aRS)-1-[2-(3,4-dichlorophenyl)acetyl]-8-[(3SR)- and (3RS)-3-hydroxypyrrolidin-1-yl]-perhydroquinoxalin-4-yl}-3-oxopropionate | 33:1 |

TABLE 4

| Compound | Selectivity κ/µ |
| --- | --- |
| 2-(3,4-Dichlorophenyl)-1-[(4aRS,8SR,8aRS)-4-methyl-8-(pyrrolidin-1-yl)-perhydroquinoxalin-1-yl]ethan-1-one | 131:1 |
| 1-[(4aRS,8SR,8aRS)-4-Butyl-8-(pyrrolidin-1-yl)-perhydroquinoxalin-1-yl]-2-(3,4-dichlorophenyl)-ethan-1-one | 177:1 |
| 1-[(4aRS,8SR,8aRS)-4-Benzyl-8-(pyrrolidin-1-yl)-perhydroquinoxalin-1-yl]-2-(3,4-dichlorophenyl)ethan-1-one | 153:1 |
| 2-(3,4-Dichlorophenyl)-1-[(4aRS,8SR,8aRS)-4-(4-methoxybenzyl)-8-(pyrrolidin-1-yl)-perhydroquinoxalin-1-yl]ethan-1-one | 16:1 |
| 2-(3,4-Dichlorophenyl)-1-{(4aRS,8SR,8aRS)-4-[(pyridin-2-yl)methyl]-8-(pyrrolidin-1-yl)perhydroquinoxalin-1-yl}ethan-1-one | 96:1 |
| 2-(3,4-Dichlorophenyl)-1-{(4aRS,8SR,8aRS)-4-[(pyridin-3-yl)methyl]-8-(pyrrolidin-1-yl)perhydroquinoxalin-1-yl}ethan-1-one | 112:1 |
| 2-(3,4-Dichlorophenyl)-1-{(4aRS,8SR,8aRS)-4-[(1H-imidazol-5-yl)methyl]-8-(pyrrolidin-1-yl)perhydroquinoxalin-1-yl]ethan-1-one | 108:1 |
| 2-(3,4-Dichlorophenyl)-1-{(4aRS,8SR,8aRS)-4-methyl-8-[(3SR)- and (3RS)-3-hydroxypyrrolidin-1-yl]-perhydroquinoxalin-1-yl}ethan-1-one | 122:1 |
| 1-{(4aRS,8SR,8aRS)-4-Benzyl-8-[(3SR)- and (3RS)-3-hydroxypyrrolidin-1-yl]perhydroquinoxalin-1-yl}-2-(3,4-dichlorophenyl)ethan-1-one | 112:1 |
| 2-(3,4-Dichlorophenyl)-1-{(4aRS,8SR,8aSR)-4-[(pyridin-3-yl)methyl]-8-[(3SR)- and (3RS)-3-hydroxypyrrolidin-1-yl]perhydroquinoxalin-1-yl}ethan-1-one | 112:1 |
| 2-(3,4-Dichlorophenyl)-1-{(4aRS,8SR,8aSR)-4-[(1H-imidazol-5-yl)methyl]-8-[(3SR)- and (3RS)-3-hydroxypyrrolidin-1-yl]perhydroquinoxalin-1-yl}ethan-1-one | 90:1 |
| <(3SR)- and (3RS)-1-{(4aRS,5RS,8aSR)-4-[2-(3,4-dichlorophenyl)acetyl]-perhydroquinoxalin-5-yl}pyrrolidin-3-yl)-2-(3,4-dichlorophenyl)acetate | 138:1 |

It was found that the compounds in each case had a high selectivity of binding to the κ receptor compared with binding to the µ receptor.

The invention claimed is:

1. A compound according to formula (I) as shown below, a stereoisomer thereof and/or a pharmaceutically acceptable salt thereof:

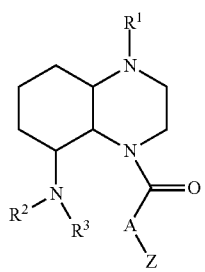

(1)

wherein:

$R^1$ is selected from the group consisting of H; $C_1$-$C_{10}$-alkyl; $C_3$-$C_{10}$-cycloalkyl; COO($C_1$-$C_{10}$-alkyl); $C_1$-$C_6$-alkoxycarbonyl; phenyl $C_1$-$C_6$ alkyl, wherein the phenyl radical can be substituted by one or more substituents selected from the group consisting of halogen, $C_1$-$C_6$-alkoxy, $NH_2$, $NH(C_1$-$C_5$-alkyl), $N(C_1$-$C_5$-alkyl)$_2$, OH, $SO_2(C_1$-$C_5$-alkyl), $SO(C_1$-$C_5$-alkyl), $CF_3$, CN, $NO_2$, $SO_2N(C_1$-$C_5$-alkyl)$_2$, $SO_2NH_2$, $SO_2NH(C_1$-$C_5$-alkyl), $SO_2NH(aryl)$, and $SO_2NH(heteroaryl)$;

C(O)($C_1$-$C_{10}$-alkyl); phenyl-$C_1$-$C_6$-acyl radical, wherein the phenyl radical can be substituted by one or more substituents selected from the group consisting of halogen, $C_1$-$C_6$-alkoxy, $NH_2$, $NH(C_1$-$C_5$-alkyl), $N(C_1$-$C_5$-alkyl)$_2$, OH, $SO_2(C_1$-$C_5$-alkyl), $SO(C_1$-$C_5$-alkyl), $CF_3$, CN, $NO_2$, $SO_2N(C_1$-$C_5$-alkyl)$_2$, $SO_2NH_2$, $SO_2NH(C_1$-$C_5$-alkyl), $SO_2NH(aryl)$, and $SO_2NH(heteroaryl)$;

monocyclic, bicyclic or tricyclic heteroaryl containing one, two, three or four heteroatoms chosen from the group consisting of N, O and S;

monocyclic, bicyclic or tricyclic heteroaryl-$C_1$-$C_6$-alkyl containing one, two, three or four heteroatoms chosen from the group consisting of N, O and S;

monocyclic, bicyclic or tricyclic heteroaryl-$C_1$-$C_6$-acyl containing one, two, three or four heteroatoms chosen from the group consisting of N, O and S;

C(O)N($C_1$-$C_{10}$-alkyl)$_2$; C(O)($C_3$-$C_{10}$-cycloalkyl); COO(aryl); COO($C_3$-$C_{10}$-cycloalkyl);

C(O)COO($C_1$-$C_{10}$-alkyl); C(O)—(CH$_2$)$_q$—COOH, wherein q is 0, 1, 2, 3 or 4; C(O)—(CH$_2$)$_r$—COO($C_1$-$C_{10}$-alkyl), wherein r is 0, 1, 2, 3 or 4; C(O)—CH(NH$_2$)—(CH$_2$)$_s$—COOH, wherein s is 0, 1, 2, 3 or 4; C(O)—CH(NH$_2$)—(CH$_2$)$_t$—COO($C_1$-$C_{10}$-alkyl), wherein t is 0, 1, 2, 3 or 4; C(O)—(CH$_2$)$_u$—CH(NH$_2$)—COOH, wherein u is 0, 1, 2, 3 or 4 and/or C(O)—(CH$_2$)$_v$—CH(NH$_2$)—COO($C_1$-$C_{10}$-alkyl), wherein v is 0, 1, 2, 3 or 4;

$R^2$ and $R^3$ are independently chosen from the group consisting of H; $C_1$-$C_{10}$-alkyl; $C_3$-$C_{10}$-cycloalkyl; and phenyl-$C_1$-$C_6$-alkyl, wherein the phenyl radical can be substituted by one or more substituents chosen from the group consisting of halogen, $C_1$-$C_5$-alkyl, $C_1$-$C_4$-alkoxy, $NH_2$, $NH(C_1$-$C_5$-alkyl), $N(C_1$-$C_5$-alkyl)$_2$, OH, COOH, COO($C_1$-$C_{10}$-alkyl), CONH$_2$, CONH($C_1$-$C_{10}$-alkyl), CON($C_1$-$C_{10}$-alkyl)$_2$, $SO_2(C_1$-$C_5$-alkyl), $SO_2NH(C_1$-$C_5$-alkyl), $CF_3$, CN and/or $NO_2$, or $R^2$ and $R^3$ form, together with the nitrogen to which they are bonded, a saturated 3- to 8-membered N-heterocycle, wherein the saturated 3- to 8-membered N-heterocycle can be substituted by one or more substituents chosen from the group consisting of OH, $C_1$-$C_4$-alkoxy, $NH_2$, $NH(C_1$-$C_5$-alkyl), $N(C_1$-$C_5$-alkyl)$_2$, COOH, COO($C_1$-$C_{10}$-alkyl), CONH$_2$, CONH($C_1$-$C_{10}$-alkyl), CON($C_1$-$C_{10}$-alkyl)$_2$, OPO$_3$H$_2$, OSO$_3$H, $SO_2(C_1$-$C_5$-alkyl), $SO_2NH(C_1$-$C_5$-alkyl), CN, OC(O)CH$_2$-aryl, which can be substituted by two Cl groups;

A is chosen from the group consisting of (CH$_2$)$_n$, wherein n is 0, 1, 2, 3, 4, 5 or 6; O; S; NH and/or aryl;

Z is chosen from the group consisting of H; $NH_2$; COOH; COO($C_1$-$C_5$-alkyl); CH(NH$_2$)COOH; $C_2$-$C_6$-acyl; formyl; and $C_1$-$C_6$-alkoxycarbonyl;

phenyl, which can be substituted by one or more substituents chosen from the group consisting of halogen, $C_1$-$C_5$-alkyl, $C_1$-$C_5$-alkyoxy, $NH_2$, $NH(C_1$-$C_5$-alkyl), $N(C_1$-$C_5$-alkyl)$_2$, OH, $SO_2(C_1$-$C_5$-alkyl), $SO(C_1$-$C_5$-alkyl), $CF_3$, CN, $NO_2$, $SO_2N(C_1$-$C_5$-alkyl)$_2$, $SO_2NH_2$, $SO_2NH(C_1$-$C_5$-alkyl), $SO_2NH(aryl)$, and $SO_2NH(heteroaryl)$;

a monocyclic, bicyclic or tricyclic aryl or heteroaryl containing one, two, three or four heteroatoms chosen from the group consisting of N, O and S, wherein the aryl or heteroaryl group can be substituted by one or more substituents chosen from the group consisting of halogen, $C_1$-$C_4$-alkoxy, $NH_2$, $NH(C_1$-$C_5$-alkyl), $N(C_1$-$C_5$-alkyl)$_2$, OH, $SO_2(C_1$-$C_5$-alkyl), $SO(C_1$-$C_5$-alkyl), $CF_3$, CN, $NO_2$, $SO_2N(C_1$-$C_5$-alkyl)$_2$, $SO_2NH_2$, $SO_2NH(C_1$-$C_5$-alkyl), $SO_2NH(aryl)$, and $SO_2NH(heteroaryl)$.

2. The compound of claim 1 represented by formula (2):

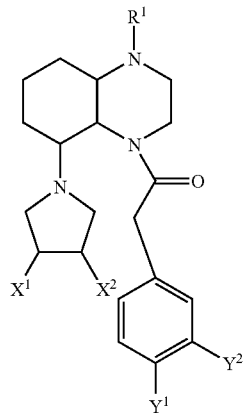

(2)

wherein:

$R^1$ is chosen from the group consisting of H; $C_1$-$C_{10}$-alkyl; $C_3$-$C_{10}$-cycloalkyl; COO($C_1$-$C_{10}$-alkyl); $C_1$-$C_6$-alkoxycarbonyl;

phenyl-$C_1$-$C_6$-alkyl, wherein the phenyl radical can be substituted by one or more substituents chosen from the group consisting of halogen, $C_1$-$C_6$-alkoxy, $NH_2$, $NH(C_1$-$C_5$-alkyl), $N(C_1$-$C_5$-alkyl)$_2$, OH, $SO_2(C_1$-$C_5$-alkyl), $SO(C_1$-$C_5$-alkyl), $CF_3$, CN, $NO_2$, $SO_2N(C_1$-$C_5$-alkyl)$_2$, $SO_2NH_2$, $SO_2NH(C_1$-$C_5$-alkyl), $SO_2NH(aryl)$, and/or $SO_2NH(heteroaryl)$;

C(O)($C_1$-$C_{10}$-alkyl); phenyl-$C_1$-$C_6$-acyl, wherein the phenyl radical can be substituted by one or more substituents chosen from the group consisting of halogen, $C_1$-$C_6$-alkoxy, $NH_2$, $NH(C_1$-$C_5$-alkyl), $N(C_1$-$C_5$-alkyl)$_2$, OH, $SO_2(C_1$-$C_5$-alkyl), $SO(C_1$-$C_5$-alkyl), $CF_3$, CN, $NO_2$, $SO_2N(C_1$-$C_5$-alkyl)$_2$, $SO_2NH_2$, $SO_2NH(C_1$-$C_5$-alkyl), $SO_2NH(aryl)$, and $SO_2NH(heteroaryl)$;

monocyclic, bicyclic or tricyclic heteroaryl containing one, two, three or four heteroatoms chosen from the group consisting of N, O and S;
monocyclic, bicyclic or tricyclic heteroaryl-$C_1$-$C_6$-alkyl containing one, two, three or four heteroatoms chosen from the group consisting of N, O and S;
monocyclic, bicyclic or tricyclic heteroaryl-$C_1$-$C_6$-acyl containing one, two, three or four heteroatoms chosen from the group consisting of N, O and S;
C(O)N($C_1$-$C_{10}$-alkyl)$_2$; C(O)($C_3$-$C_{10}$-cycloalkyl); COO($C_1$-$C_{10}$-alkyl); COO(aryl); COO($C_3$-$C_{10}$-cycloalkyl);
C(O)COO($C_1$-$C_{10}$-alkyl), C(O)—(CH$_2$)$_q$—COOH, wherein q is 0, 1, 2, 3 or 4, C(O)—(CH$_2$)$_r$—COO($C_1$-$C_{10}$-alkyl), wherein r is 0, 1, 2, 3 or 4, C(O)—CH(NH$_2$)—(CH$_2$)$_s$—COOH, wherein s is 0, 1, 2, 3 or 4, C(O)—CH(NH$_2$)—(CH$_2$)$_t$—COO($C_1$-$C_{10}$-alkyl), wherein t is 0, 1, 2, 3 or 4, C(O)—(CH$_2$)$_u$—CH(NH$_2$)—COOH, wherein u is 0, 1, 2, 3 or 4, and/or C(O)—(CH$_2$)$_v$—CH(NH$_2$)—COO($C_1$-$C_{10}$-alkyl), wherein v is 0, 1, 2, 3 or 4;
$X^1$ and $X^2$ are independently chosen from the group consisting of H, OH, NH$_2$, NH($C_1$-$C_5$-alkyl), N($C_1$-$C_5$-alkyl)$_2$, COOH, COO($C_1$-$C_{10}$-alkyl), CONH$_2$, CONH($C_1$-$C_{10}$-alkyl), CON($C_1$-$C_{10}$-alkyl)$_2$, OPO$_3$H$_2$, OSO$_3$H, SO$_2$($C_1$-$C_5$-alkyl), SO$_2$NH($C_1$-$C_5$-alkyl), $C_1$-$C_4$-alkoxy, OC(O)CH$_2$-aryl, which can be substituted by two Cl groups;
$Y^1$ and $Y^2$ are independently chosen from the group consisting of H, halogen, $C_1$-$C_5$-alkyl, $C_1$-$C_5$-alkoxy, NH$_2$, NH($C_1$-$C_5$-alkyl), NH(aryl), NH(heteroaryl), N($C_1$-$C_5$-alkyl)$_2$, OH, SO$_2$($C_1$-$C_5$-alkyl), SO($C_1$-$C_5$-alkyl), CF$_3$, CN, NO$_2$, SO$_2$N($C_1$-$C_5$-alkyl)$_2$, SO$_2$NH$_2$, SO$_2$NH($C_1$-$C_5$-alkyl).

3. The compound of claim 1 represented by formula (3):

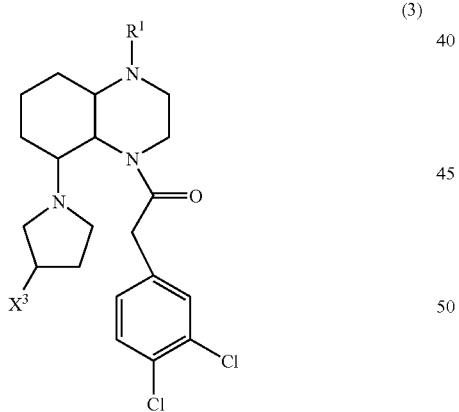

(3)

wherein:
$R^1$ is chosen from the group consisting of H; $C_1$-$C_5$-alkyl; Phenyl-$C_1$-$C_4$-alkyl, wherein the phenyl radical can be substituted by one or more substituents chosen from the group consisting of Cl, OH and $C_1$-$C_4$-alkoxy;
N-heteroaryl $C_1$-$C_4$-alkyl wherein the N-heteroaryl radical is chosen from the group consisting of pyridinyl, imidazolyl, pyrimidinyl, pyrazinyl and pyrrolyl;
$C_2$-$C_5$-acyl; formyl; benzoyl; COO($C_1$-$C_5$-alkyl); COO(aryl); C(O)—(CH$_2$)$_q$—COOH, wherein q is 0, 1, 2, 3 or 4 and/or C(O)—(CH$_2$)$_r$—COO($C_1$-$C_5$-alkyl), wherein r is 0, 1, 2, 3 or 4;

$X^3$ is chosen from the group consisting of H, OH, benzyl and/or OC(O)CH$_2$-aryl, which can be substituted by two Cl groups.

4. The compound of claim 1, represented by formula (4):

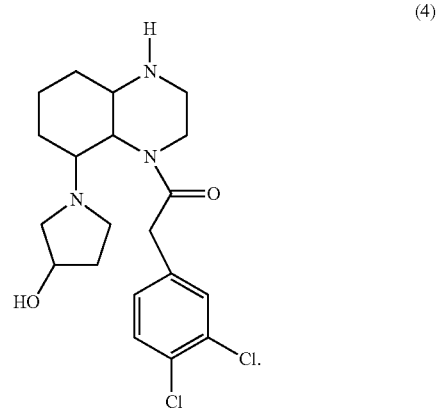

(4)

5. The compound of claim 1, represented by formula (6):

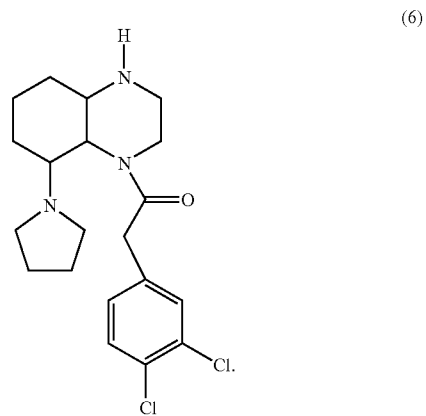

(6)

6. A process for the preparation of a compound according to formula (I) of claim 1, which comprises the following steps:

a) cyclization of nitromethane and glutaraldehyde to give 2-nitrocyclohexane-1,3-diol;

b) amination of 2-nitrocyclohexane-1,3-diol to give N,N'-dibenzyl-2-nitrocyclohexane-1,3-diamine;

c) reduction of the nitro group of N,N'-dibenzyl-2-nitrocyclohexane-1,3-diamine to give $N^1$,$N^3$-dibenzylcyclohexane-1,2,3-triamine;

d) reaction of $N^1$,$N^3$-dibenzylcyclohexane-1,2,3-triamine with dialkyl oxalate to give 1-benzyl-5-(benzylamino)octahydroquinoxaline-2,3-dione;

e) debenzylation of 1-benzyl-5-(benzylamino)octahydroquinoxaline-2,3-dione to give 5-amino-1-benzyloctahydroquinoxaline-2,3-dione;

f) alkylation of 5-amino-1-benzyloctahydroquinoxaline-2,3-dione to give 1-benzyl-5-(pyrrolidin-1-yl)octahydroquinoxaline-2,3-dione;

g) reduction of the perhydroquinoxalinedione ring of 1-benzyl-5-(pyrrolidin-1-yl)-octahydroquinoxaline-2,3-dione to give 1-benzyl-5-(pyrrolidin-1-yl)decahydroquinoxaline;

h) acylation of 1-benzyl-5-(pyrrolidin-1-yl)decahydroquinoxaline to give 1-[4-benzyl-8-(pyrrolidin-1-yl)decahydroquinoxalin-1(2H)-yl]-2-(3,4-dichlorophenyl)ethan-1-one; and i) optionally, debenzylation of 1-4-benzyl-8-(pyrrolidin-1-yl)decahydroquinoxalin-1(2H)-yl]-2-(3,4-dichlorophenyl)ethan-1-one to give other compounds of formula (1).

* * * * *